United States Patent
Goode et al.

(10) Patent No.: US 10,653,440 B2
(45) Date of Patent: May 19, 2020

(54) TIP FOR LEAD EXTRACTION DEVICE

(75) Inventors: Louis B. Goode, Cranberry Township, PA (US); Chun Kee Lui, Monroeville, PA (US); Robert Booker, Vandergrift, PA (US)

(73) Assignee: Cook Medical Technologies LLC, Bloomington, IN (US)

( * ) Notice: Subject to any disclaimer, the term of this patent is extended or adjusted under 35 U.S.C. 154(b) by 46 days.

(21) Appl. No.: 11/867,967

(22) Filed: Oct. 5, 2007

(65) Prior Publication Data
US 2008/0071341 A1  Mar. 20, 2008

Related U.S. Application Data

(63) Continuation-in-part of application No. 11/404,176, filed on Apr. 14, 2006, now abandoned.
(Continued)

(51) Int. Cl.
*A61B 17/50* (2006.01)
*A61N 1/05* (2006.01)
(Continued)

(52) U.S. Cl.
CPC .... *A61B 17/3207* (2013.01); *A61B 17/32002* (2013.01); *A61B 17/32053* (2013.01);
(Continued)

(58) Field of Classification Search
CPC ............ A61B 17/3207; A61B 17/3468; A61B 17/32053; A61B 2017/320044;
(Continued)

(56) References Cited

U.S. PATENT DOCUMENTS

| 2,261,230 A | 11/1941 | Cox et al. ...................... 128/310 |
| 3,132,549 A | 5/1964 | Lee .................................. 81/57 |

(Continued)

FOREIGN PATENT DOCUMENTS

| EP | 0 807 412 A1 | 11/1997 | ............. A61B 17/32 |
| EP | 1 820 458 A1 | 8/2007 | ............. A61B 17/22 |

(Continued)

OTHER PUBLICATIONS

Albee, F., "Bone Surgery with Machine Tools," Scientific American, Apr. 1936, pp. 178-181.

*Primary Examiner* — Julian W Woo
(74) *Attorney, Agent, or Firm* — Brinks Gilson & Lione

(57) ABSTRACT

A tip engageable with an elongated sheath member for extracting an implanted elongated structure, such as a cardiac lead, from an obstruction in a body vessel of a patient. The tip includes a tip body having a proximal end, a distal end, and a passageway extending therethrough. The tip body proximal end is engageable with the distal end of the sheath member distal end. The passageway of the tip is aligned with the passageway of the sheath such that the implanted structure is receivable therein. The tip body distal end includes a segment tapering toward a leading edge. A disrupter element, such as a plurality of helices, is disposed along the outer surface of the tip body distal end. The disruptor element is configured for non-cuttingly disrupting the obstruction as the tip is advanced over the implanted structure.

17 Claims, 17 Drawing Sheets

Related U.S. Application Data

(60) Provisional application No. 60/671,858, filed on Apr. 15, 2005.

(51) Int. Cl.
| | | |
|---|---|---|
| *A61B 17/3207* | (2006.01) | |
| *A61B 17/32* | (2006.01) | |
| *A61B 17/3205* | (2006.01) | |
| *A61B 17/34* | (2006.01) | |

(52) U.S. Cl.
CPC .......... *A61B 17/3468* (2013.01); *A61N 1/056* (2013.01); *A61B 2017/320044* (2013.01); *A61B 2017/320741* (2013.01); *A61N 2001/0578* (2013.01)

(58) Field of Classification Search
CPC . A61B 2017/320741; A61B 17/3205–320783; A61B 17/32002–320036; A61B 2017/320024–32004; A61B 2017/320716–320791; A61N 1/056–0575; A61N 2001/0578–0585
USPC .......... 606/129, 108, 159, 207, 45; 607/127, 607/115
See application file for complete search history.

(56) References Cited

U.S. PATENT DOCUMENTS

| | | | |
|---|---|---|---|
| 3,519,046 A | 7/1970 | Pierce | 145/66 |
| 3,756,090 A | 9/1973 | Melia et al. | |
| 4,030,503 A | 6/1977 | Clark, III | 128/304 |
| 4,084,594 A | 4/1978 | Mosior | 128/311 |
| 4,174,858 A | 11/1979 | Brooks | 285/7 |
| 4,574,800 A * | 3/1986 | Peers-Trevarton | A61N 1/056 606/1 |
| 4,576,162 A | 3/1986 | McCorkle | |
| 4,643,190 A | 2/1987 | Heimberger | |
| 4,943,289 A | 7/1990 | Goode et al. | |
| 4,988,347 A | 1/1991 | Goode et al. | |
| 5,011,482 A | 4/1991 | Goode et al. | |
| 5,013,310 A | 5/1991 | Goode et al. | |
| 5,052,402 A | 10/1991 | Bencini et al. | 128/751 |
| 5,092,848 A | 3/1992 | deCiutiis | 604/170 |
| 5,122,134 A | 6/1992 | Borzone et al. | 606/80 |
| 5,207,683 A | 5/1993 | Goode et al. | |
| 5,304,189 A * | 4/1994 | Goldberg | A61B 17/32075 606/159 |
| 5,363,726 A | 11/1994 | Smith | 81/57.29 |
| 5,423,806 A | 6/1995 | Dale et al. | |
| 5,447,534 A * | 9/1995 | Jammet | 607/127 |
| 5,507,751 A | 4/1996 | Goode et al. | |
| 5,549,615 A * | 8/1996 | Hocherl | A61N 1/057 606/1 |
| 5,591,187 A | 1/1997 | Dekel | |
| 5,632,749 A | 5/1997 | Goode et al. | |
| 5,651,781 A | 7/1997 | Grace | 606/1 |
| 5,697,936 A | 12/1997 | Shipko et al. | |
| 5,769,858 A | 6/1998 | Pearson et al. | |
| 5,807,399 A * | 9/1998 | Laske | A61N 1/057 606/108 |
| 5,814,044 A | 9/1998 | Hooven | |
| 5,830,221 A | 11/1998 | Stein et al. | 606/151 |
| 5,830,231 A | 11/1998 | Geiges, Jr. | 606/205 |
| 5,913,857 A | 6/1999 | Ritchart et al. | |
| 5,913,867 A | 6/1999 | Dion | 606/180 |
| 5,980,515 A * | 11/1999 | Tu | 606/41 |
| 5,980,545 A | 11/1999 | Pacala et al. | 606/170 |
| 5,984,939 A | 11/1999 | Yoon | |
| 5,993,467 A | 11/1999 | Yoon | |
| 6,010,476 A | 1/2000 | Saadat | 604/22 |
| 6,099,537 A | 8/2000 | Sugai et al. | |
| 6,135,947 A * | 10/2000 | Watanabe et al. | 600/178 |
| 6,136,005 A | 10/2000 | Goode et al. | |
| 6,190,353 B1 | 2/2001 | Makower et al. | |
| 6,283,511 B1 | 9/2001 | Kamp | 285/391 |
| 6,332,886 B1 | 12/2001 | Green et al. | 606/80 |
| 6,419,974 B1 | 7/2002 | Silva et al. | |
| 6,503,261 B1 | 1/2003 | Bruneau et al. | 606/159 |
| 6,656,195 B2 | 12/2003 | Peters et al. | 606/159 |
| 6,687,548 B2 | 2/2004 | Goode | |
| 6,712,826 B2 | 3/2004 | Lui | |
| 6,712,855 B2 * | 3/2004 | Martin et al. | 623/20.34 |
| 6,783,533 B2 | 8/2004 | Green et al. | 606/80 |
| 2002/0007190 A1* | 1/2002 | Wulfman | A61B 17/320725 606/167 |
| 2002/0138091 A1* | 9/2002 | Pflueger | A61B 10/0266 606/170 |
| 2002/0143358 A1 | 10/2002 | Domingo et al. | 606/190 |
| 2002/0172923 A1* | 11/2002 | Strong et al. | 433/165 |
| 2002/0188307 A1* | 12/2002 | Pintor et al. | 606/159 |
| 2003/0040787 A1* | 2/2003 | Flynn et al. | 607/122 |
| 2004/0143287 A1 | 7/2004 | Konstantino et al. | 606/194 |
| 2004/0260336 A1 | 12/2004 | Braun | |
| 2005/0107816 A1 | 5/2005 | Pingleton et al. | 606/185 |
| 2005/0149096 A1 | 7/2005 | Hilal et al. | 606/191 |
| 2005/0273125 A1 | 12/2005 | Opie | |
| 2006/0235431 A1 | 10/2006 | Goode et al. | |
| 2006/0253179 A1 | 11/2006 | Goode et al. | |
| 2008/0045986 A1* | 2/2008 | To et al. | 606/159 |
| 2008/0071342 A1 | 3/2008 | Goode et al. | 607/122 |

FOREIGN PATENT DOCUMENTS

| | | |
|---|---|---|
| FR | 2 625 429 A1 | 7/1989 |
| WO | WO 02/36022 A1 | 5/2002 |

* cited by examiner

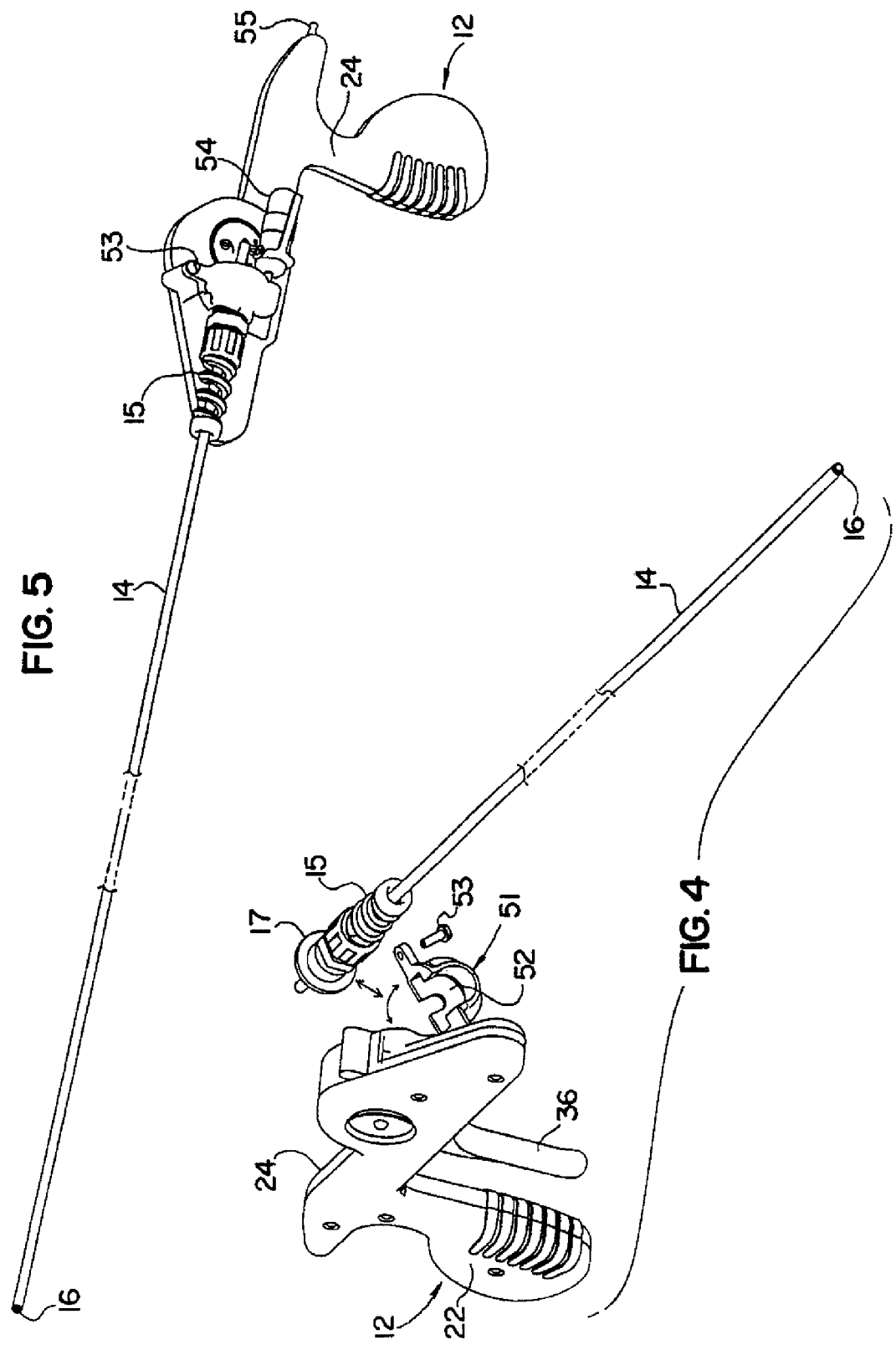

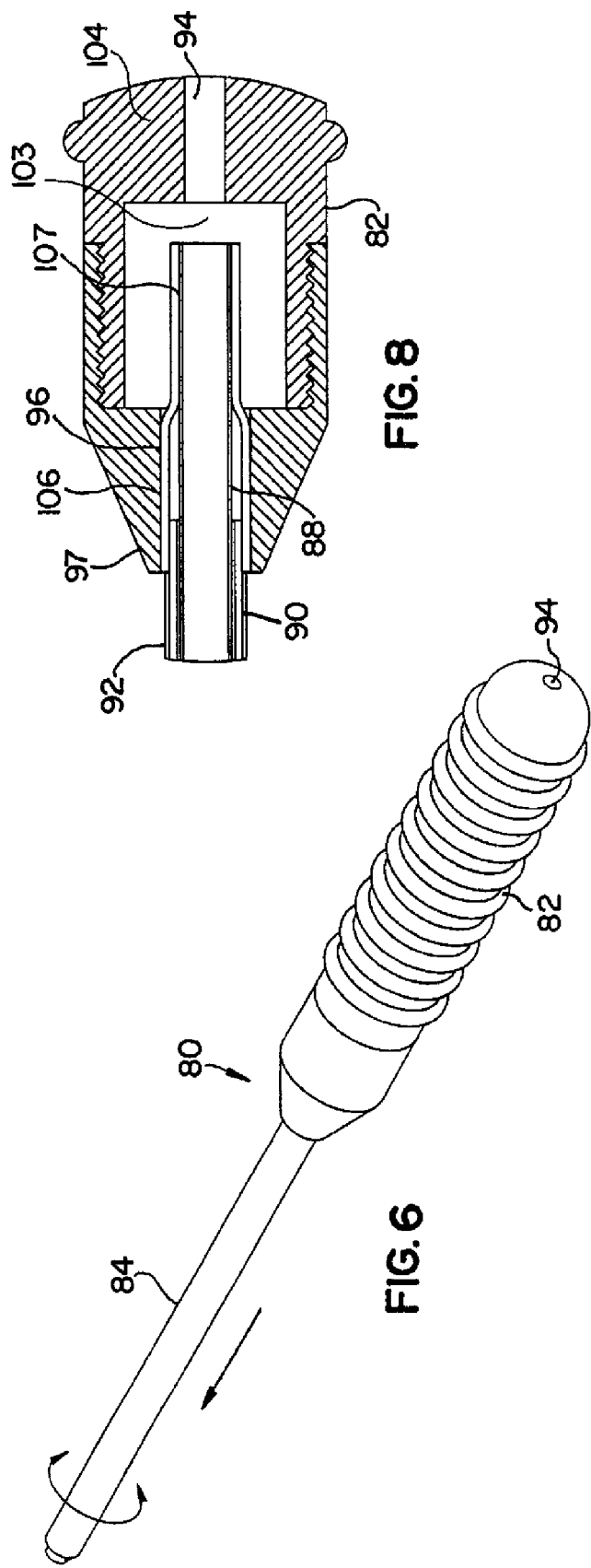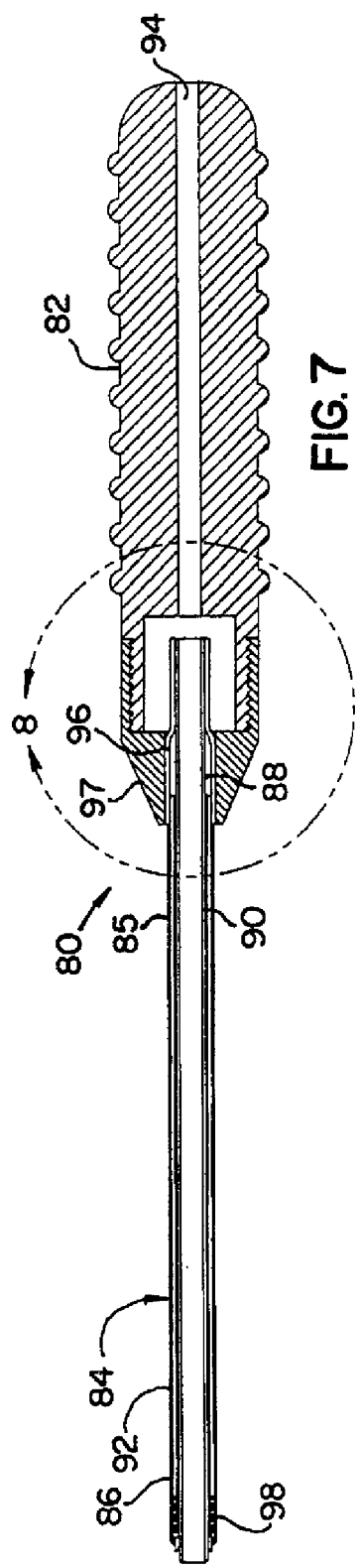

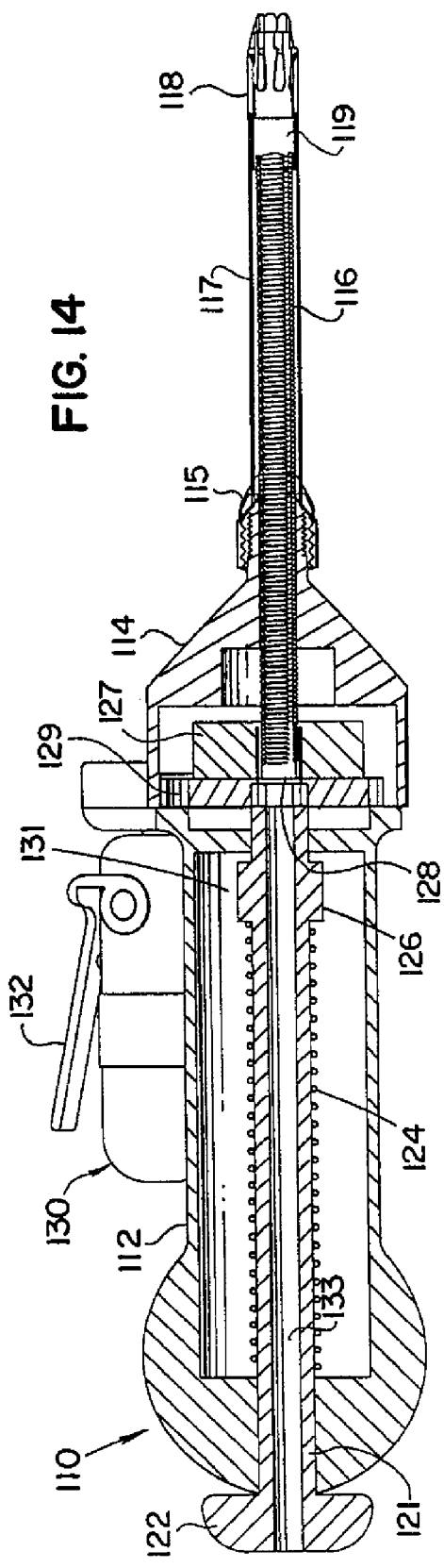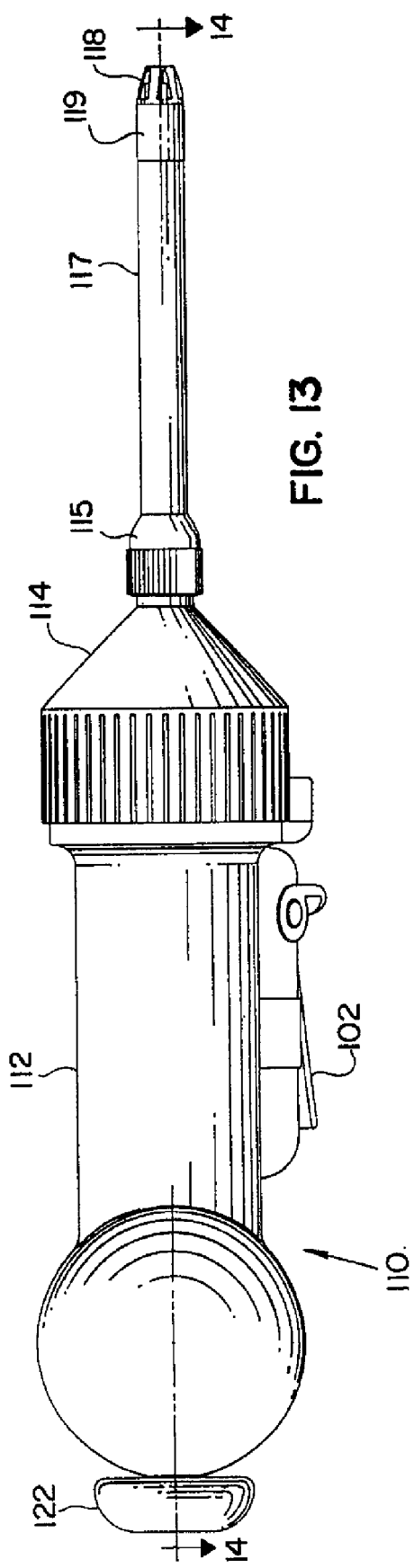

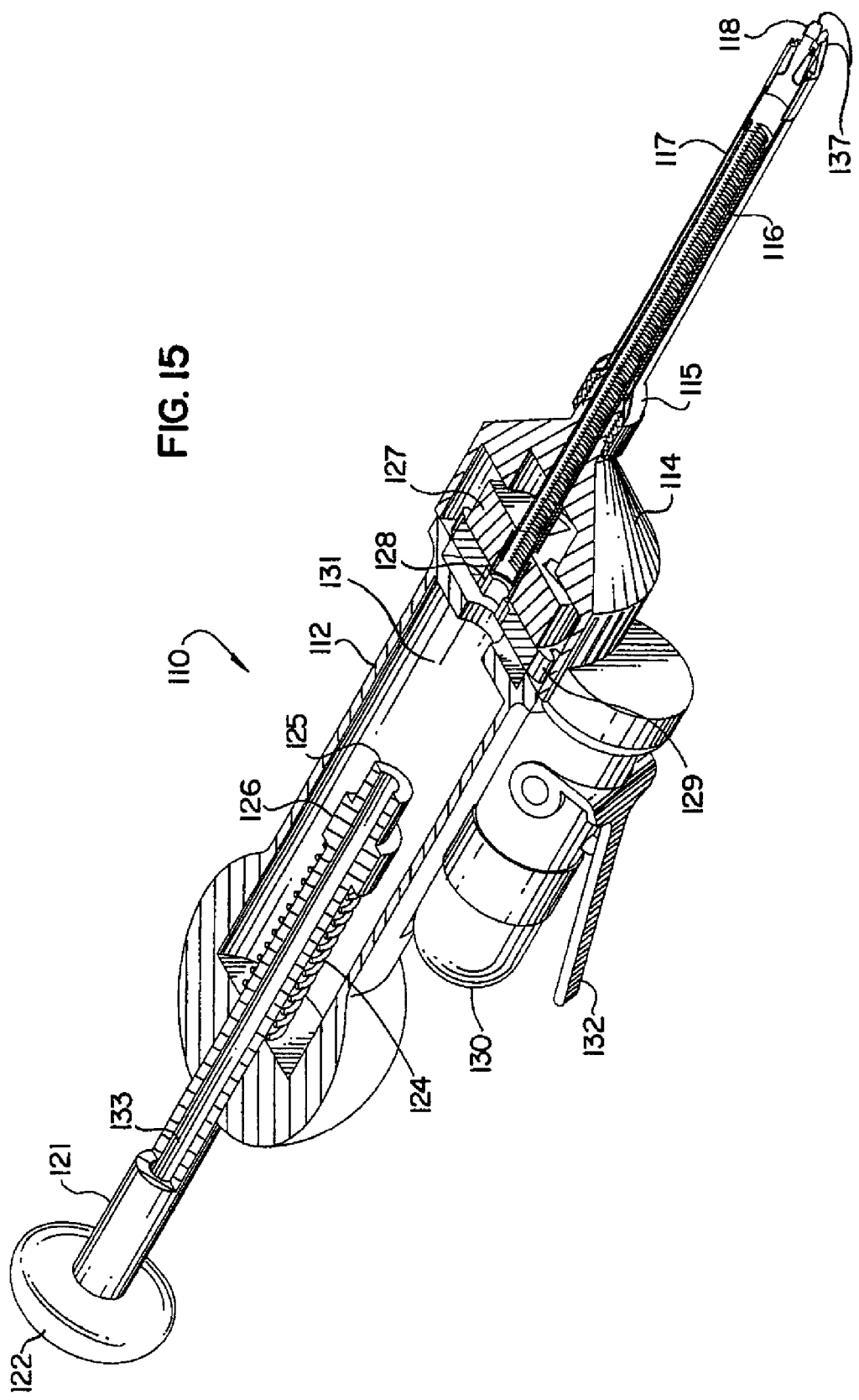

TIP FOR LEAD EXTRACTION DEVICE

RELATED APPLICATION

The present patent document is a continuation-in-part application of U.S. patent application Ser. No. 11/404,176, filed Apr. 14, 2006, now abandoned, which claims the benefit of the filing date under 35 U.S.C. § 119(e) of Provisional U.S. Patent Application Ser. No. 60/671,858, filed Apr. 15, 2005. Each of the foregoing applications is hereby incorporated by reference.

BACKGROUND

1. Technical Field

This invention relates generally to devices for use in the medical arts. More particularly, the invention relates to a tip for use with a device for separating an implanted elongated structure, such as an implanted electrical pacemaker or defibrillator lead, from encapsulating biological tissue.

2. Background Information

A variety of medical treatments and surgical methods entail implanting an elongated structure in the body of a human or veterinary patient. Examples of such elongated structures include catheters, sheaths and cardiac electrical leads (such as pacemaker leads and defibrillator leads), as well as a variety of other devices. Over time, it can become necessary or desirable to remove the implanted elongated structure from the body of the patient. However, if the elongated structure has been implanted for an extended period of time, encapsulating biological tissue can grow around the elongated structure, making it difficult to remove the structure from the encapsulating tissue.

A heart pacemaker is typically implanted in a subcutaneous tissue pocket in the chest wall of a patient. A pacemaker lead extends from the pacemaker through a vein into a chamber of the patient's heart. The pacemaker lead commonly includes a conductor, such as an electrical wire coil, for conducting electrical signals (such as stimulating and/or sensing signals) between the pacemaker and the heart. Leads for defibrillators are generally similar to pacemaker leads, and are positioned about the heart. Defibrillator leads may be affixed either internally or externally of the heart.

Some leads include one or more coaxial or lateral helical wire coils having a hollow inner passageway that extends the entire length of the wire coil or coils. Other leads may be made with a cable without a hollow inner passageway. The wire coils are surrounded by an electrically insulating material such as a flexible tube, sheath or coating. The insulating material, generally formed of silicone or polyurethane, serves to simultaneously protect the wire coils from body fluids and insulate the wire coils from one another.

While cardiac electrical leads typically have a useful life of many years, over time such leads may become encapsulated by fibrotic tissue against the heart itself or the wall of the vein, or against other surrounding tissue. Encapsulation is especially encountered in areas where the velocity of the flow of blood is low. The fibrotic tissue can be very tough, which makes it difficult to remove the lead from the area of the heart without causing trauma to the area. When small diameter veins through which a pacemaker lead passes become occluded with fibrotic tissue, separation of the lead from the vein can cause severe damage to the vein, including the possible dissection or perforation of the vein. In such cases, separation of the lead from the vein is usually not possible without restricting or containing movement of the lead, i.e., fixing the lead in position with respect to the patient, in particular, with respect to the patient's vein.

To avoid this and other possible complications, some useless pacemaker or other leads are simply left in the patient when the pacemaker or defibrillator is removed or replaced. However, such a practice can incur the risk of an undetected lead thrombosis, which can result in stroke, heart attack, or pulmonary embolism. Such a practice can also impair heart function, as plural leads can restrict the heart valves through which they pass.

There are many other reasons why removal of a useless lead may be desirable. For example, if there are too many leads positioned in a vein, the vein can be obstructed to the extent that fluid flow through the vein is severely compromised. In addition, multiple leads can be incompatible with one another, thereby interfering with the pacing or defibrillating function. An inoperative lead can migrate during introduction of an adjacent second lead, and mechanically induce ventricular arrhythmia. Other potentially life-threatening complications can require the removal of the lead as well. For example, removal of an infected pacemaker lead may be desirable so as to avoid conditions such as septicemia or endocarditis.

Surgical removal of a heart lead in such circumstances often involves open heart surgery. However, open heart surgery is accompanied by significant risk and cost to the patient, as well as a potential for unintended complications. A variety of methods and apparatuses have been devised as alternatives to open heart surgery for heart lead removal. Several of these methods and apparatuses are described in related patents, such as U.S. Pat. No. 5,697,936, titled "Device for Removing an Elongated Structure Implanted in Biological Tissue"; U.S. Pat. No. 5,507,751, titled "Locally Flexible Dilator Sheath"; U.S. Pat. No. 5,632,749, titled "Apparatus for Removing an Elongated Structure Implanted in Biological Tissue"; U.S. Pat. No. 5,207,683, titled "Apparatus for Removing an Elongated Structure Implanted in Biological Tissue"; U.S. Pat. No. 4,943,289, titled "Apparatus for Removing an Elongated Structure Implanted in Biological Tissue"; U.S. Pat. No. 5,011,482, titled "Apparatus for Removing an Elongated Structure Implanted in Biological Tissue"; U.S. Pat. No. 5,013,310, titled "Method and Apparatus for Removing an Implanted Pacemaker Lead"; U.S. Pat. No. 4,988,347, titled "Method and Apparatus for Separating a Coiled Structure from Biological Tissue"; U.S. Pat. No. 5,423,806, titled "Laser Extractor for an Implanted Object"; U.S. Pat. No. 6,419,974, titled "Radio Frequency Dilator Sheath", and U.S. Pat. Nos. 6,687,548 and 6,712,826, each titled "Apparatus for Removing an Elongated Structure Implanted in Biological Tissue", among others. Each of the aforementioned patents is incorporated by reference as if fully set forth herein.

Most of the aforementioned patents describe manual, or mechanical, devices that are used for removing an implanted structure, such as a pacemaker lead. Others describe newer non-mechanical techniques, such as laser extraction and radio frequency extraction. These newer techniques have been effective in many cases when the amount and/or placement of fibrous growth that surrounds the implanted lead renders manual extraction difficult or impossible. One example of an effective device that uses radio frequency extraction to enable the physician to cut away the heavy growth is the PERFECTA® electrosurgical dissection sheath, available from Cook Vascular Incorporated, of Leechburg, Pa. The PERFECTA® sheath utilizes an intermittent discrete RF dissecting arc between bipolar electrodes located at the sheath's distal end. This sheath enables the physician to separate, with directed precision, a transvenous lead from its fibrous binding attachments.

Although the prior art devices have been found to be reasonably effective in many situations, physicians continue to encounter particularly difficult situations in which existing extraction devices provide unsatisfactory or inconsistent results. Due to the multiplicity of factors that may contribute to the difficulty in extracting an implanted lead, a technique that may be effective in one instance, may not provide similarly successful results in another instance. For example, manual devices normally are provided with single or telescoping flexible sheaths. Such sheaths, generally formed from a polymer, have the flexibility to enable the sheath to traverse tortuous pathways in the vessel. However, such sheaths may lack sufficient strength to cut through particularly tough tissue growth and calcification around the implanted lead. Laser and radio frequency devices normally utilize metallic sheaths. Such sheaths provide a good deal of strength to enable the sheath to cut through fibrous growths. However, some growths are resistant to metallic sheaths, and these sheaths may also lack the flexibility desired to maneuver tortuous pathways.

It would be desirable to provide a device and tip structure that is effective for removing implanted leads from a vessel, that is easy to operate, and that is versatile enough to overcome many of the obstacles that may be encountered in such operations with existing devices.

BRIEF SUMMARY

The present invention addresses the problems of the prior art extraction devices. In one form thereof, the invention comprises a tip engageable with an elongated sheath member for extracting an implanted structure from an obstruction in a body vessel of a patient. The tip includes a tip body having a proximal end, a distal end, and a passageway extending therethrough. The tip body proximal end is engageable with the distal end of the sheath member distal end. The passageway of the tip body is alignable with a passageway of the sheath member, such that the implanted structure is receivable therein. The tip body distal end includes a segment tapering toward a leading edge. A disrupter element is disposed along an outer surface of the tip body distal end, and is disposed proximal of at least the leading edge of the tapered segment. The disrupter element is configured for non-cuttingly disrupting the obstruction as the tip is advanced over the implanted structure.

In another form thereof, the invention comprises an apparatus for extracting an elongate implanted structure from an obstruction within a vessel of a patient. An elongate sheath member comprises a lumen sized to receive the elongated implanted structure therein, the elongate sheath member being sufficiently flexible to track over the implanted structure within the vessel. A tip is disposed at the distal end of the sheath member comprising an outer surface having at least one disrupter element disposed at least partially thereabout. The tip has a leading edge configured for non-cutting engagement with the obstruction such that advancement of the sheath over the implanted structure and into the obstruction causes the at least one disrupter element to push aside and separate the obstruction from the implanted structure without a forward cutting action, and wherein contact by the tip with a wall of the vessel and/or an outer surface of the implanted structure is substantially atraumatic.

BRIEF DESCRIPTION OF THE DRAWINGS

FIG. 4 is a view showing the handle and sheath of the lead extraction device prior to assembly;

FIG. 5 is a view of the reverse side of an embodiment of a lead extraction device including a power supply;

FIG. 6 is a perspective view of another embodiment of a lead extraction device according to the present invention;

FIG. 7 is a longitudinal sectional view of the lead extraction device of FIG. 6;

FIG. 8 is an enlarged view of a portion of the device as shown in FIG. 7, illustrating the joinder of the sheath assembly and the handle;

FIG. 13 is a side view of another embodiment of a lead extraction device according to the present invention;

FIG. 14 is a sectional view taken along lines 14-14 of FIG. 13;

FIG. 15 is a sectional view of the lead extraction device of FIG. 13, with the striker shown in a retracted position;

DETAILED DESCRIPTION OF THE DRAWINGS AND THE PRESENTLY PREFERRED EMBODIMENTS

Figure 1:
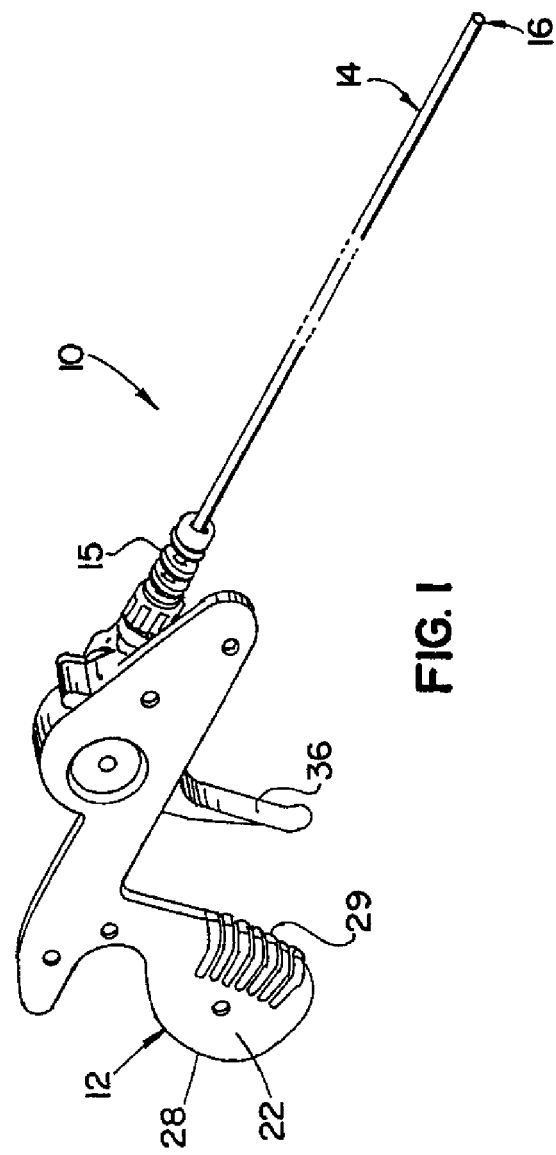
FIG. 1 is a perspective view of one embodiment of a lead extraction device of the present invention.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention relates to an extraction device for extracting an elongated structure that has previously been implanted into a patient, and more particularly, to a tip for use with an extraction device. In the following discussion, the terms "proximal" and "distal" will be used to describe the opposing axial ends of the device, as well as the axial ends of various component features of the device. The term "proximal" is used in its conventional sense to refer to the end of the device (or component thereof) that is closest to the operator during use of the device. The term "distal" is used in its conventional sense to refer to the end of the device (or component) that is at the greatest distance from the operator, or that is initially inserted into the patient.

The implanted elongated structure targeted for removal may comprise a cardiac lead. A cardiac lead, as the term is used herein, refers to a lead that is used in connection with a heart-related device. Non-limiting examples of cardiac leads that may be removed by the inventive device include pacemaker leads, defibrillator leads, coronary sinus leads, and left ventricular pacing leads. When the device is used to remove a cardiac pacemaker lead, the distal end of the cardiac lead will normally be located within the vascular system of the patient, and in particular, within a chamber of the patient's heart (such as in an atrium or ventricle of the heart). When the implanted elongated structure is a defibrillator lead, the distal end of the structure may be located either in or about the heart of the patient. The distal ends of other types of implanted elongated structures targeted for removal may not necessarily be near the heart.

In addition to cardiac leads, the invention may also be used in the removal of other devices or leads, such as neurological pacing and stimulation leads. A non-limiting list of still other structures that can be removed by the inventive device includes implanted catheters, sheaths, cannulae and the like. For convenience, the following discussion will refer to the removal of a cardiac lead, such as a pacemaker or a defibrillator lead. However it should be understood that this is no way intended to be a limitation on the scope of the invention, and that the device may be suitable for removal of at least the other elongated structures referred to above.

Typically, a cardiac lead comprises an inner core, comprising a cable or a coil, surrounded by a layer of insulating material. As explained previously, some cardiac leads have a lumen extending therethrough, while others (i.e., "lumenless" leads) do not. The extraction devices of the present invention are useful for extracting implanted leads having a lumen, as well as lumenless leads. When an inventive device is to be used for removal of a cardiac lead, those skilled in the art will appreciate that the lead should initially be severed from the control device, such as the pacemaker or defibrillator, prior to any attempts to remove the lead. The control device will normally have a much larger diameter than the remainder of the lead, and thus only an unreasonably large dilator sheath could fit over the control device.

FIG. 1 depicts a perspective view of a preferred embodiment of a lead extraction device 10 for use in separating an encapsulated elongated structure, such as a cardiac electrical lead, from biological tissue. When a cardiac lead is implanted in a vessel, all or a portion of the elongated structure of the lead may become encapsulated over time by fibrotic biological tissue that grows against the wall of the vessel or surrounding tissue. The inventive lead extraction device 10 is particularly useful for removing the encapsulated cardiac lead from the vein of a patient. In the embodiment shown, lead extraction device 10 comprises a handle 12, a sheath 14 extending distally from handle 12, and a cutting tip 16 at a distal end of the sheath. As shown in the figure, an optional strain relief 15 may be provided at the proximal end of sheath 14 to inhibit kinking of the sheath.

Figure 2:
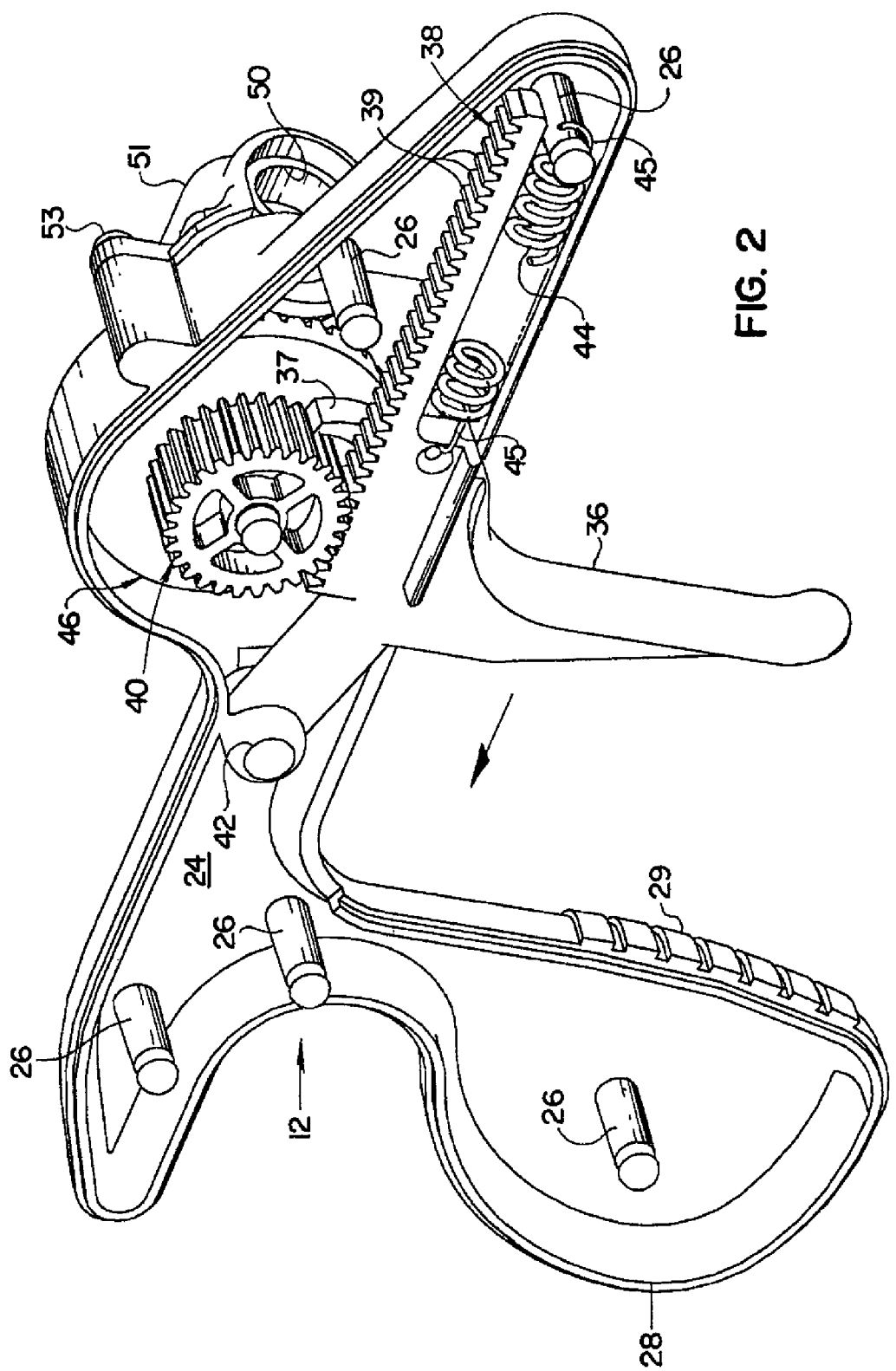
FIG. 2 is a perspective view of the handle of the lead extraction device of FIG. 1, with a portion of the outer wall removed to illustrate the inner components of the handle.

FIG. 2 is a perspective view of handle 12. Outer handle wall 22 has been removed from this figure to allow visualization of the internal features of the handle. Handle 12 comprises opposing wall members 22 (FIG. 1) and 24. Wall members 22, 24 are connected via a snap fit or other conventional mechanism. In the embodiment shown, wall member 24 includes a plurality of transverse pegs 26 that are received in corresponding receptacles (not shown) in wall member 22 when the walls are snapped or otherwise fitted together in well-known fashion. Preferably, handle 12 has an ergonomically shaped grip 28, as shown in the figures. If desired ergonomic grip 28 may also include a plurality of ribs 29 spaced along a hand-engaging surface of grip 28.

Figure 3:
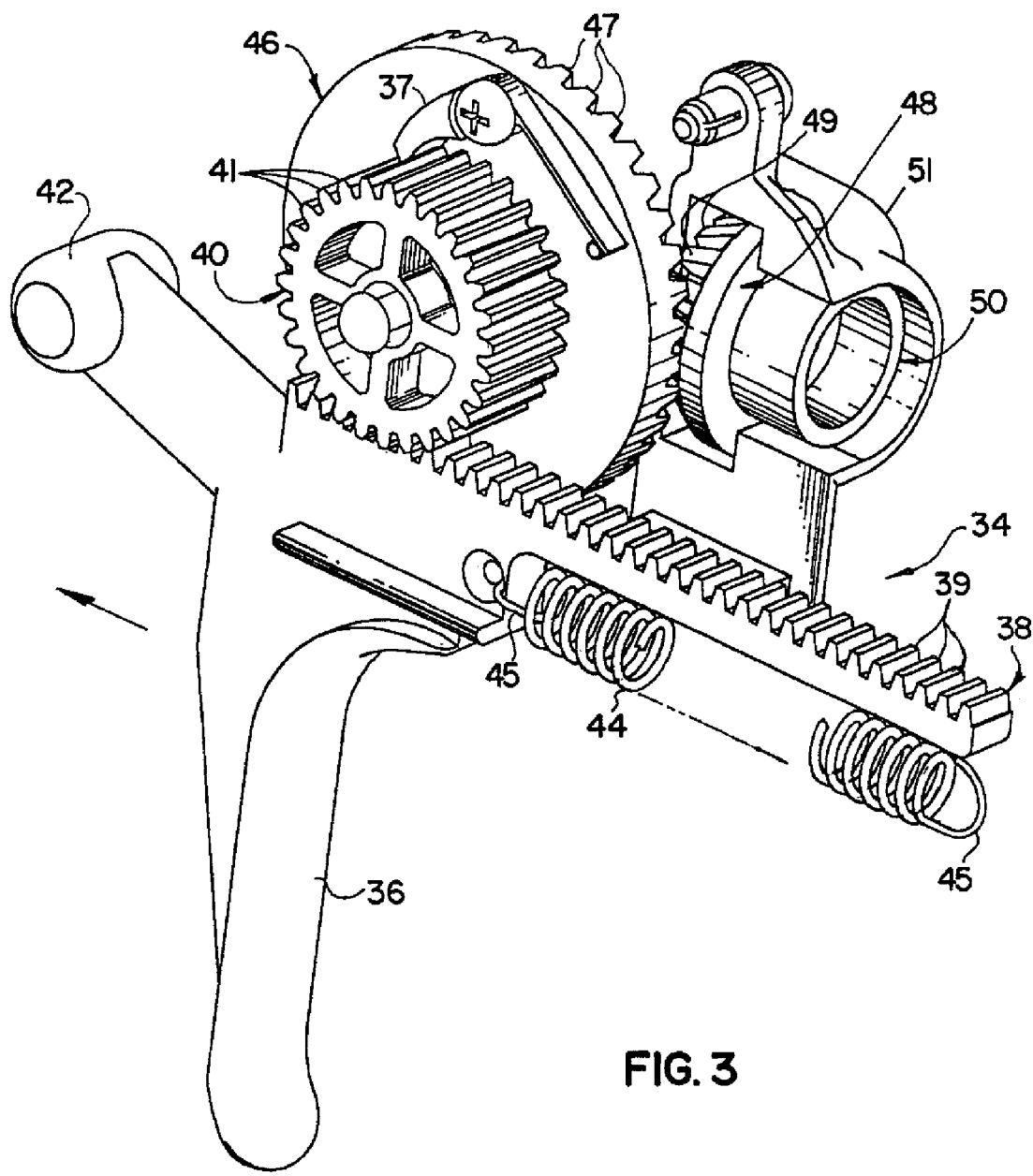
FIG. 3 is a view of the translation device removed from the handle of the lead extraction device.

In the embodiment of the handle shown in FIGS. 2 and 3, handle 12 includes a translation mechanism 34. For ease of viewing, translation mechanism 34 is removed from the wall members of handle 12 in FIG. 3. Translation mechanism 34 utilizes a rack and gear structure to translate linear motion generated upon pull of an actuator, such as trigger 36, into rotational motion on the part of shaft 14. Translation mechanism 34 includes a rack 38 having a plurality of teeth 39 as shown. Rack 38 is engaged with trigger 36, such that upon the operator pulling trigger 36 in the proximal direction (as indicated by the arrow), rack 38 likewise is urged linearly in the proximal direction.

An external spur gear 40, having a plurality of teeth 41, is aligned with rack 38 such that spur gear teeth 41 mesh with rack teeth 39. Linear movement of rack teeth 39 therefore causes spur gear 40, and thus teeth 41, to rotate in the direction shown. A pawl 37 may be provided to inhibit undesired (counter-clockwise) rotation of the gear. Pawl 37 may also be configured to create ratcheting action upon movement of rack 38 and spur gear 40, and to provide an audible confirmation of the rotation of the spur gear. A stabilizing arm 42 extending in a proximal direction from rack 38 may be provided to maintain proper orientation of rack 38 in handle 12, and to ensure smooth movement of the trigger without bending or flexing when pulled under a load. Preferably, a spring 44 is affixed at one end to rack 38 and at the other end to housing wall peg 26 (distal of rack 38), for urging trigger 36 back to the position shown in FIG. 2 upon relaxation of the tension resulting from the trigger pull by the operator. Spring 44 may be retained in handle 12 by any conventional means, such as hooks 45.

Spur gear 40 is affixed to large bevel gear 46, in a manner such that rotation of spur gear 40 causes a corresponding rotation of large bevel gear 46. Large bevel gear 46 includes a plurality of teeth 47 on a side of large bevel gear 46 opposite spur gear 40. Small bevel gear 48 is rotationally aligned with large bevel gear 46 in conventional fashion, such that large bevel gear teeth 47 mesh with small bevel gear teeth 49 as illustrated. Teeth 47 and 49 are aligned in conventional fashion for such bevel gears, in this case at an angle of about 90 degrees. As a result, the direction of rotation is translated via said gears along the 90 degree angle. Hub 50 is affixed to the side of small bevel gear 48 opposite teeth 49 for rotation in accordance with the rotation of small bevel gear 48. Hub 50 is sized and shaped to securely receive a proximal end of sheath 14, by conventional means such as adhesion, friction and/or threading.

Preferably, sheath 14 is removably affixed in lead extraction device 10 in a manner such that it may be selectively affixed to, or removed from, device 10. FIG. 4 illustrates one preferred manner in which sheath 14 may be removably affixed in lead extraction device 10. Hub 50 is not visible in the orientation of FIG. 4. In this embodiment, wall member 24 includes a pivotable wall portion 51 that may be pivoted to the open position as shown, and sheath 14 is provided with a flange 17 at the proximal end of the sheath 14 to seat the sheath in the hub. When the sheath is affixed in hub 50, flange 17 is snugly received against a surface 52 of pivotable portion 51. When portion 51 is pivoted into the closed position, a conventional latching mechanism, such as a screw 53 is provided to maintain pivotable portion 51 in the closed position (FIG. 5), thereby retaining sheath 14 in handle 12. Those skilled in the art will appreciate that there are numerous other ways in which the sheath may be held in the handle, and that the particular removable affixation mechanism described herein is not crucial to the invention.

Thus, as has been shown, sheath 14 may be selectively attached to, and detached from, handle 12. In this manner, sheath 14 and tip 16 may be simply removed from handle 12 following a lead extraction procedure, and replaced with another sheath and tip for use in a subsequent operation. Similarly, by utilizing detachable components, sheath 14 and tip 16 may be removed and replaced with a sheath and tip of a larger, or smaller, size as may be appropriate for removal of the particular lead involved in the procedure. Typically, lead extraction device 10 may also include a conventional free floating outer sheath (not shown) that telescopes over sheath 14 in well known fashion. Those skilled in the art are well aware of the use of telescoping outer sheaths for such purposes, and further discussion of this free floating outer sheath is not necessary for an understanding of the features of the present invention.

During manual operation of device 10 shown in FIGS. 1-4, the operator pulls trigger 36 in the linear direction shown. As discussed, this action drives, or translates, the linear motion of the trigger pull to rotary movement of hub 50, thereby causing rotation of sheath 14. Rack and gear structures are well known in the art. The remaining features of the translation mechanism not described herein are conventional, and need not be further explained or illustrated to enable one skilled in the art to utilize the mechanism for the purposes described. In addition, those skilled in the art will appreciate that there are numerous other ways in which a manual device can be structured such that an action generated by an operator, such as the trigger pull described herein, may be translated to rotary motion. Although the rack and gear structure described and shown herein is preferred, it is not intended to represent the only way that such translation can be accomplished. All such techniques within the knowledge of one skilled in the art are considered within the scope of the invention.

FIG. 5 illustrates another feature of the invention. In this embodiment, the rack and gear structure, as well as the trigger of FIGS. 1-4, have been eliminated. These features have been replaced with a power source, such as drive motor 54. The power source may comprise any conventional source suitable for driving the rotation of the hub, such as a source for generating electrical, battery or pneumatic power. A suitable actuator, such as button 55, may be provided to selectively activate, and deactivate, drive motor 54. Upon actuation, the drive motor operates in well known fashion to cause sheath 14 to rotate. Although the translational mechanism and trigger have been removed from the embodiment shown in FIG. 5, this need not be the case. Rather, device 10 can be provided with both a manual operation (such as via trigger 36 and translation mechanism 34) and a powered operation (such as via drive motor 54). In this case an operator can selectively utilize either, or both, of these features during a particular lead extraction procedure.

As illustrated in FIGS. 1 and 4-5, a tip 16 is provided at the distal end of sheath 14. Sheath 14 may be constructed in a manner such that distal tip 16 is an integral part with the sheath; however, it is preferred that tip 16 comprises a discrete element joined to the distal end of sheath 14. Typically, the sheath is formed of a flexible composition to enable the sheath to be threaded through a vessel to free the lead from an obstruction. However, it is generally desired to provide a tip formed of a composition having greater strength than the sheath, so that it is better able to cut or otherwise disrupt the obstruction. Non-limiting examples of suitable tips are illustrated in FIGS. 18 to 27.

Another feature of the invention comprises a device 80 for removing or otherwise extracting an elongated implanted structure, such as a lead, from a body vessel. Device 80 is illustrated in FIG. 6. In the embodiment shown, device 80 comprises a handle 82 and a sheath assembly 84. Device 80 is structured such that sheath assembly 84 may be manually urged forwardly in the distal direction (as indicated by the linear arrow in FIG. 6) and/or twisted in a rotary direction (as indicated by the curved arrow in FIG. 6) when used to extract an elongated structure, such as a lead, from a vessel. An inner passageway 94 extends through extraction device 80 in conventional fashion to receive the lead to be extracted.

One preferred manner of retaining sheath assembly 84 in handle 82 is shown in FIGS. 7 and 8. Further details of the sheath assembly are visible in enlarged FIGS. 9-12. As illustrated, sheath assembly 84 has a proximal end 85 and a distal end 86. In the embodiment shown, sheath assembly 84 comprises an inner sheath 88 positioned within an intermediate sheath 90. Preferably, sheath assembly 84 further comprises an outer sheath 92 for housing inner sheath 88 and intermediate sheath 90.

Figure 9:
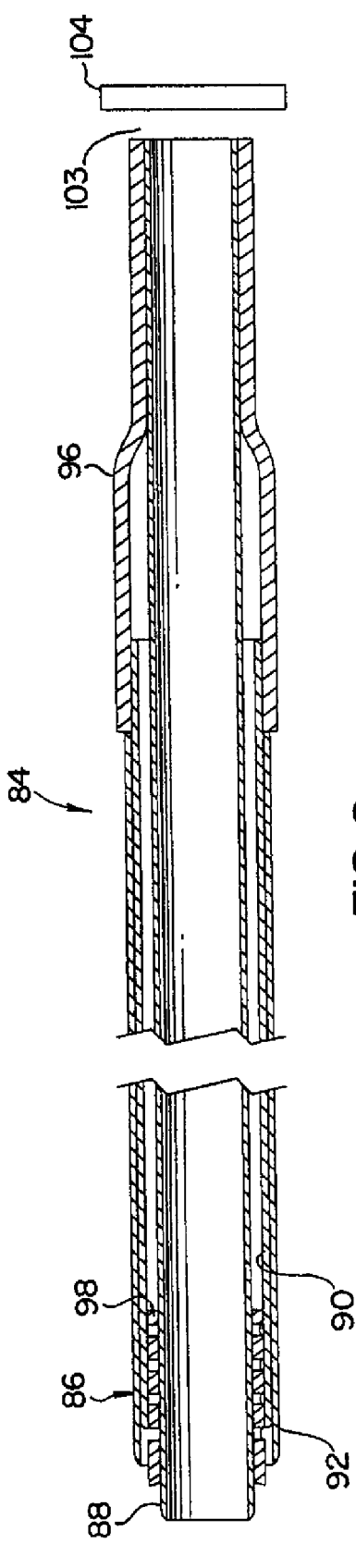
FIG. 9 is an enlarged sectional view of the sheath assembly, taken along lines 9-9 of FIG. 10.
Figure 10:
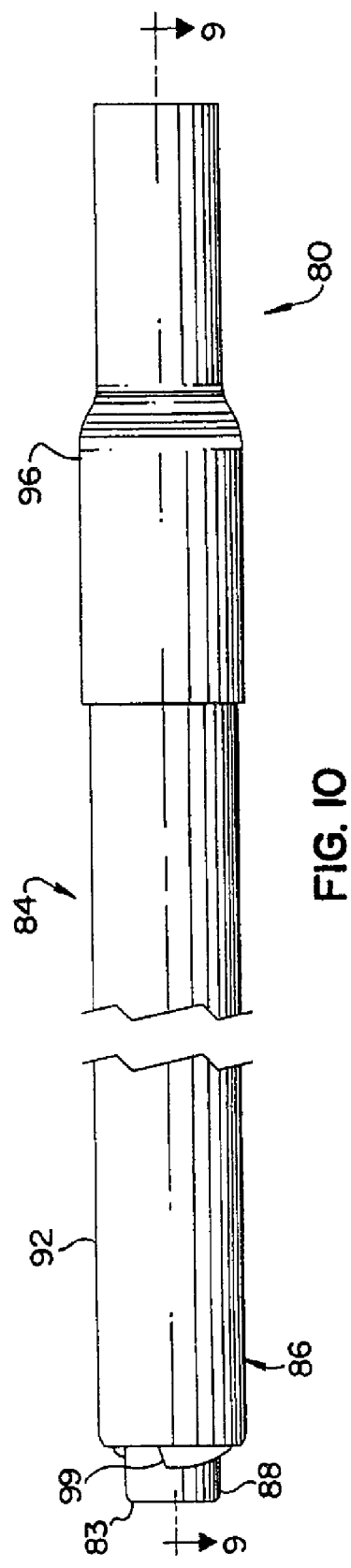
FIG. 10 is an enlarged side view of the sheath assembly portion of the lead extraction device of FIG. 6.
Figure 12:
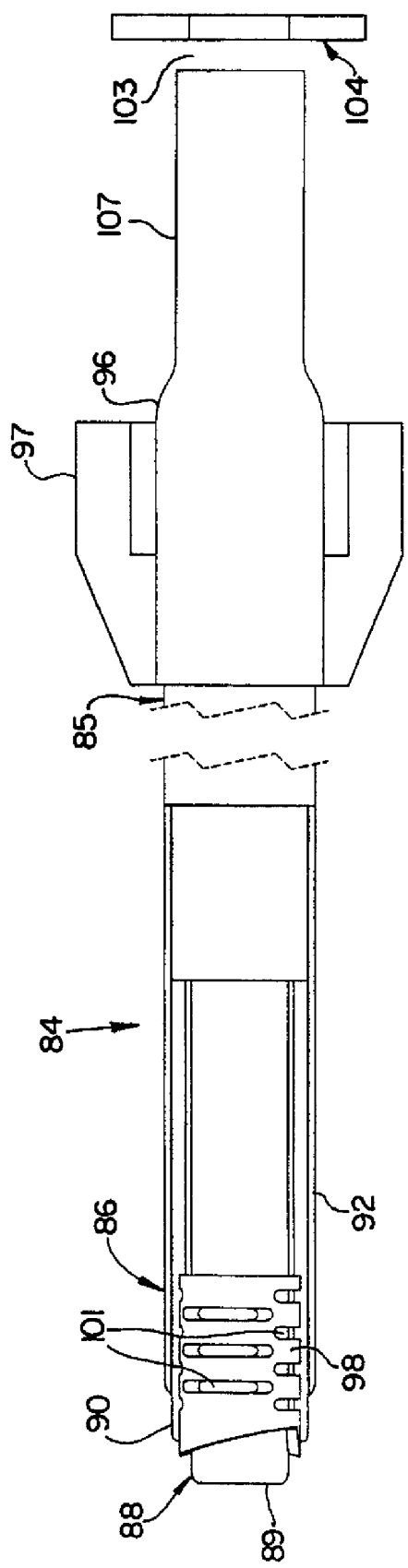
FIG. 12 is a view, partially in section, taken along line 12-12 of FIG. 11 showing the cutting tip, and also illustrating the handle nose portion.

Sheath assembly 84 also includes an element for providing spring action for inner sheath 88, such as flexible boot 96. As best shown in FIG. 9, the proximal end of the intermediate sheath 90 is bonded or otherwise affixed at the inner surface of the distal portion 106 of boot 96. The outer surface of boot distal portion 106 is preferably fixedly engaged with handle nose piece 97 (FIGS. 8, 12). Thus, the intermediate sheath, distal boot portion and nose piece are fixed in the device, and are immovable relative to each other. The proximal end of inner sheath 88 is bonded or otherwise affixed to proximal portion 107 of boot 96 in a manner such that the inner sheath and proximal boot and are not capable of independent movement relative to one another, and are free floating in the device. In this context, "free floating" means that inner sheath 88 and boot proximal portion 107 are rotatable and/or axially movable in the device. In particular, inner sheath 88 is rotatable and/or axially movable relative to fixed intermediate sheath 90, and boot proximal end 107 is rotatable and/or free floating relative to the handle.

Boot 96 should, of course, be flexible enough to permit relatively free and easy axial and/or rotational "free floating" movement of the inner sheath 88 and boot proximal end 107 when the lead extraction device encounters an obstruction during a lead extraction procedure. The boot should also have sufficient memory to enable it to return to its original, or neutral, position shown in the figures when no obstruction is present, or when the obstruction has been successfully cut. Preferably, the boot is formed from, e.g., a silicone or a polymeric composition having the requisite capabilities for spring action as described. Alternatively, the boot may comprise other known elastic or spring means, such as a stainless steel extension spring that is sized to fit the respective proximal ends of both the inner and outer sheaths. Those skilled in the art can readily select an appropriate composition and/or arrangement to provide the flexible feature of the boot.

In the preferred embodiment shown, the outer sheath 92 is not affixed to the device, but rather, works in a telescopic manner as it rides on the inner and intermediate sheaths 88, 90. Outer sheath 92 can be advanced beyond the distal end of cutting tip 98 in a distal direction if desired. The length of outer sheath 92, and the point at which it seats on the device when in its most proximal position, controls the degree of exposure of the inner sheath beyond the distal end of cutting tip 98.

Figure 11:
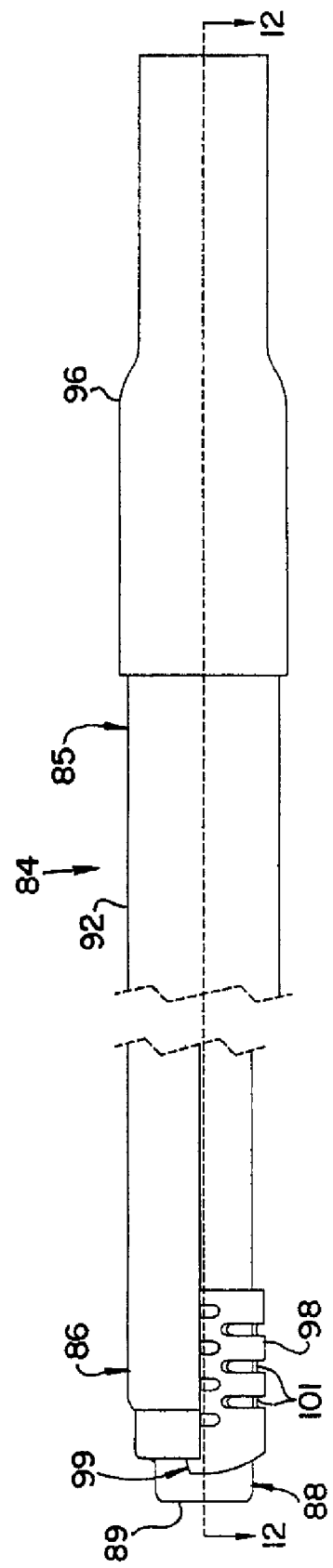
FIG. 11 is a side view of the sheath assembly, partially broken away to illustrate the cutting tip.

A cutting tip 98 is affixed at the distal end of intermediate sheath 90. Preferably, cutting tip 98 is affixed to the inner surface of the distal end of intermediate sheath 90, as best shown in FIGS. 11 and 12. In a preferred embodiment, cutting tip 98 is provided with a plurality of slots 101, and the tip is bonded onto the inner surface of intermediate sheath 90, e.g., by thermal bonding in a heat shrink envelope. During the heat bonding operation, as sheath 90 begins to melt, a portion of the sheath flows through slots 101 of cutting tip 98. After sheath 90 cools and hardens following removal of the heat, cutting tip 98 becomes tightly bonded to sheath 90 through slots 101. Thermal bonding is a well known technique in the medical arts, and further discussion of this technique is not necessary to an understanding of the invention.

Although thermal bonding is a preferred manner for affixing cutting tip 98 to sheath 90, those skilled in the art will appreciate that other known ways of bonding or otherwise affixing a tip to a substrate may be substituted. For example, the cutting tip can be provided with attachment members, such as barbs, along the proximal length of the cutting tip. As another alternative, the cutting tip can be provided with a roughened outer surface for facilitating attachment with the inner surface of the sheath. Those skilled in the art can readily determine other appropriate attachment mechanisms for a particular case.

Cutting tip 98 is preferably formed of a metal or a metal alloy. Non-limiting examples of tip compositions include stainless steel (preferably SAE No. 303-304), titanium and nitinol. In a preferred embodiment, the length of the metal cutting tip does not exceed about 0.375 inch (9.5 mm), however, those skilled in the art will appreciate that cutting tips of other sizes may be substituted in a particular case. In the preferred embodiment of FIGS. 9-12, cutting tip 98 is provided with a plurality of cutting teeth 99. Cutting teeth 99 preferably extend in the distal direction from the main body of cutting tip 98. In the preferred embodiment shown, tip 98 includes two distally-extending cutting teeth 99 (only one of which is visible in the figures), each provided at a radially opposite side of the distal end of the device. Although the tip composition and arrangement described herein is preferred, those skilled in the art can readily determine other tip compositions appropriate for a particular use.

During use of the device, axial movement of the inner sheath in the proximal direction is limited by stop member 104. Preferably, stop member 104 is made from plastic, and is molded, machined, bonded, snapped, etc. into the handle of the lead extraction device. Stop member 104 is best shown in FIG. 8, and is shown schematically in FIGS. 9 and 12. As illustrated, there is a slight gap 103 between the proximal end of boot 96 and stop member 104, to allow for movement of inner sheath 88 in the proximal direction when the device encounters an obstruction. The length of gap 103 is sized so as to limit proximal movement of the distal tip of the inner sheath, such that cutting teeth 99 extend only incrementally in the distal direction beyond distal end 89 of inner sheath 88 when the inner sheath has retracted to its furthest proximal point. Distal extension of the cutting teeth is thus limited either by the inner sheath stop, as described, and/or by the length of the outer sheath.

The length of gap 103 also represents the distance that the tip of the inner sheath extends distally beyond the cutting tip when the inner sheath is in a neutral position (no obstruction encountered). Thus, as shown in the figures, distal end 89 of inner sheath 88 normally extends in the distal direction beyond the respective distal ends of intermediate sheath 90 and outer sheath 92, as well as beyond the distal end of the respective cutting teeth 87. As stated, the respective sheaths, and the stop, are dimensioned and arranged such that the distal tip 89 of inner sheath 88 cannot retract beyond the distal end of the intermediate sheath 90 when an obstruction is encountered. When this occurs, the inner sheath distal tip 89 slides in the proximal direction until it is flush with the distal end of intermediate sheath 90.

The lengths of the respective sheaths in sheath assembly 84 are thus arranged such that when the assembly is in the neutral position, the distal end of outer sheath 92 preferably shields inner sheath 88 and the cutting tip 98 of intermediate sheath 90. When the device is used to remove an implanted elongated structure, such as a cardiac lead, the device initially rails along the lead until an obstruction is encountered by the distal, or leading, end 89 of the inner sheath. At this time, the flexibility of boot 96 allows the inner sheath 88 to slide in the proximal direction in response to the obstruction. At the same time, lead extraction device 80 may be manually urged by the operator in the forward (distal) direction through the obstruction by pushing and/or twisting the device. The stop member 104 limits movement of the inner sheath 88 in the proximal direction, such that the distal tips of the cutting teeth are substantially flush with, or extend incrementally distal to, distal end 89 of inner sheath 88. During the retreat of inner sheath 88 in the proximal direction, intermediate sheath 90 and outer sheath 92 remain in a generally fixed position. Since the boot communicates with the respective proximal ends of both the intermediate and inner sheaths when the inner sheath is pushed in the proximal direction, the elastic or spring property of the boot causes a spring action at the proximal end of the inner sheath, thereby urging inner sheath 88 back to its extended position shown in the figures once the obstruction has been overcome.

FIGS. 13-17 illustrate another embodiment of a lead extraction device 110. As shown in FIG. 13, device 110 comprises a generally cylindrical housing 112, a nose mechanism 114, a nose cap 115, a sheath 117, a restrictor sleeve 119 and a distal cutting tip 118. Nose mechanism 114 is joined at its proximal end to housing 112 by any conventional means, such as a snap connection, a screw connection, or a friction fit, and may be maintained in the position shown in the figures by nose cap 115. Nose cap 115 also receives the proximal end of sheath 117, and provides a transition between nose mechanism 114 and sheath 117. The distal end of sheath 117 receives the proximal end of restrictor sleeve 119. Restrictor sleeve 119 provides a transition between sheath 117 and the proximal end of distal tip 118, whereupon the proximal end of distal cutting tip 118 is received in restrictor sleeve 119. A passageway 133 (FIG. 14) extends longitudinally through device 110, for receiving the elongated structure to be extracted, such as a cardiac lead.

In the embodiment shown, tip 118 is provided with a plurality of fingers 137 that project in the distal direction. If desired, tip 118 can be structured such that the respective distal ends of fingers 137 are slightly movable in conjunction with movement of knob 122 from an open position having a diameter that slightly exceeds the diameter of the lead to be extracted, to a closed position wherein the fingers wrap around and grip the lead. In addition to the configuration shown, tip 118 may have any of the tip configurations illustrated in FIGS. 18-26 described below, or any other conventional tip configuration used for cutting or disrupting a lead from encapsulating tissue.

Figure 16:
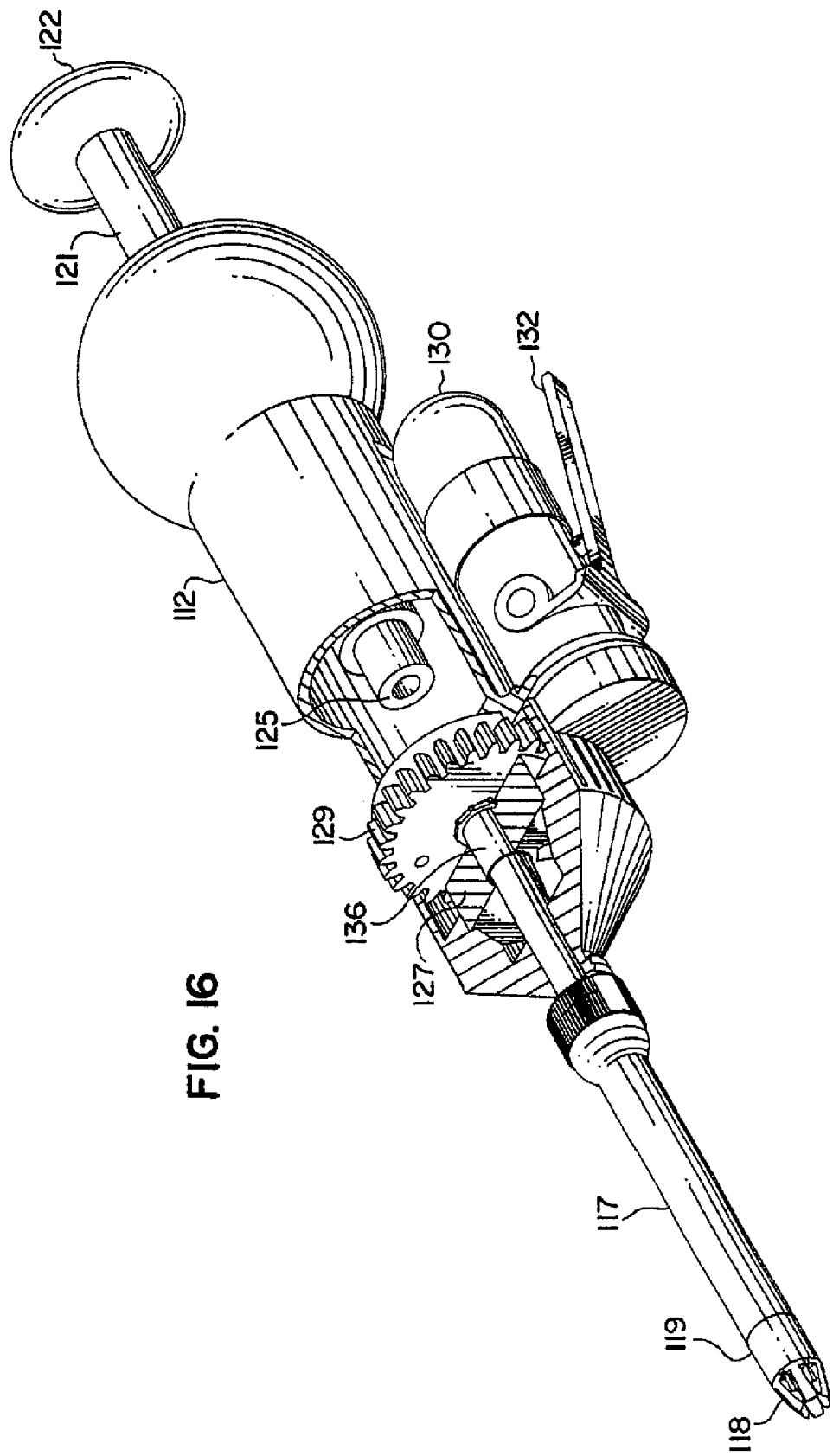
FIG. 16 is a perspective view of the lead extraction device of FIG. 13, with portions cut away to illustrate internal operating features of the device.
Figure 17:
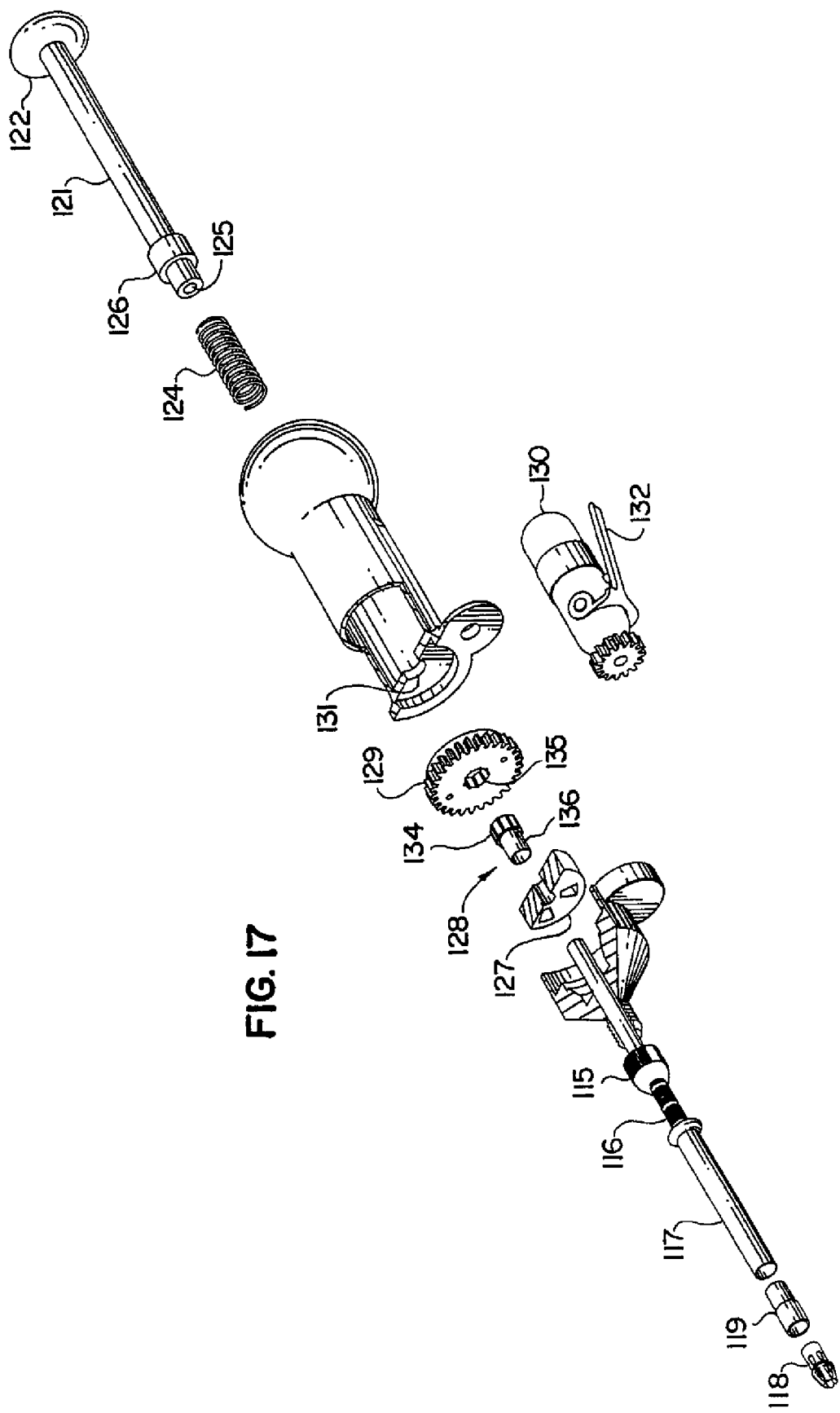
FIG. 17 is an exploded view of the lead extraction device of FIG. 13.

Further details of device 110, as well as its preferred mode of operation, may be readily observed in FIGS. 15-17. FIG. 15 is a sectional view similar to that of FIG. 14, with the striker 121 and striker knob 122 shown in a retracted position. FIG. 16 is a view of device 110 similar to that of FIG. 15, but cut-away in a manner to illustrate internal operating features of the device. FIG. 17 is an exploded view of device 110.

Striker 121 is provided for manual operation of device 110. Striker 121 comprises a striker knob 122 at its proximal end, a bias means such as striker spring 124 distal of knob 122, a stop collar 126 distal of spring 124, and a striker leading edge 125. Leading edge 125 is sized such that it extends through an opening 131 at the distal end of housing 112. Distal movement of leading edge 125 is limited by stop collar 126. A striker flange 128 is positioned for selective contact with striker leading edge 125. Preferably, striker flange 128 includes a larger diameter proximal portion 134 and a smaller diameter distal portion 136, as best shown in FIG. 17. In this embodiment, larger diameter proximal portion 134 is received within a lumen of drive gear 129. Preferably, larger diameter portion 134 includes a splined outer surface, which surface is sized and configured to engage reciprocal splines 135 along the drive gear lumen. Smaller diameter portion 136 is received in the lumen of flange retainer 127. Flange retainer 127 is formed of a generally flexible material such as silicone, and is positioned interiorly of nose mechanism 114, as best shown in FIG. 14. In the embodiment shown, the proximal end of an elongated member, such as drive coil 116, is received within small diameter distal end 136 of flange 128. The distal end of drive coil 116 extends through outer sheath 117 and restrictor sleeve 119, such that it is securely received within an interior space of distal tip 118.

To operate device 110 manually, striker knob 122 is initially withdrawn in the proximal direction, as illustrated in FIGS. 15 and 16. As a result, striker spring 124 and stop collar 126 are withdrawn proximally in a manner such that a spring tension is created in striker spring 124. Upon release of striker knob 122, the tension in drive spring 124 is released, thereby driving striker leading edge 125 in the distal direction such that it strikes the proximal end of striker flange 128. This impact drives the striker flange and the flange retainer in the distal direction, which in turn, urges drive coil 116 and tip 118 distally. Thus, the force derived from the release of the striker knob is translated in linear fashion through the device to distal cutting tip 118. Tip 118 is urged forwardly incrementally a fixed distance of, e.g., about 0.125 inch (3.2 mm). The device can be structured to allow distal movement of the tip distances other than 0.125 inch (3.2 mm), however, this is a preferred incremental distance for a sequential cut when cutting the lead away from a vessel. The distance at which the tip is structured to move in the distal direction responsive to a single pull and release of knob 122 is largely controlled and limited by the position of stop collar 126 on striker 121. Thus, in the embodiment shown, stop collar 126 limits the advance of striker leading edge 125, such that leading edge 125 can advance only the controlled distance of 0.125 inch (3.2 mm), which in turn advances striker flange 128 a like distance. This is best shown in FIG. 14, wherein further distal movement of the stop collar is prevented by the distal end of housing 112. Those skilled in the art will appreciate that stop collar 126 can be positioned at different axial locations along striker 121 if incremental cuts of other than 0.125 inch (3.2 mm) are desired for a particular cutting operation.

In a preferred embodiment, device 110 is also provided with a power supply 130 to enable powered operation of the device. Power supply 130 may comprise any conventional source of power suitable for such use, such as electrical, battery or pneumatic power. For powered operation, an activation switch 132 may be provided for activating the power supply, and/or for selectively converting device 110 between manual and power operation. Activation of the power supply causes rotation of drive gear 129. Due to the splined or like interconnection of drive gear 129 and striker flange 128, rotation of the drive gear causes rotation of the striker flange, which in turn, causes rotation of drive coil 116 and tip 118. Thus, those skilled in the art will appreciate that cutting tip 118, drive coil 116, flange retainer 127, flange 128 and drive gear 129 are rotationally engaged to one another in a manner such that they are axially and rotationally movable as a unit, which unit is freely movable within housing 112, outer sheath 117 and restrictor sleeve 119. As a result, when power supply 130 is activated, this inner assembly will rotate from the drive gear to the tip.

Thus, as described, device 110 is capable of selectively utilizing either manual or powered operation. Manual operation provides a hammer-like action wherein the tip is incrementally urged forwardly, and then withdrawn, in linear fashion. This action may be repeated as many times as desired. Powered operation provides rotary action to the tip. Depending upon the nature of the encapsulation of the lead encountered, some obstructions may respond better to the hammer-like action of the tip provided by manual operation, while others may respond better to the rotary tip action provided by the powered operation. In still other instances, the encapsulation may respond better to a sequential operation of, e.g., manual, and then power, operation, or vice versa. As a result, device 110 provides sufficient versatility to address numerous different encapsulation situations that may be encountered.

Although the embodiment of lead extraction device 110 described hereinabove includes the option of utilizing either manual or powered operation, or both, the device need not include both options. Thus, the device can be structured to provide only manual hammer-like operation, or only powered operation. When only manual operation is desired, power supply 130 may be eliminated, along with drive gear 129. In this event, only minimal structural modifications will be required to compensate for the lack of a drive gear. On the other hand, when only power operation is desired, the striker mechanism 121 may be eliminated.

A device for removing an implanted elongated structure, such as a cardiac lead, according to the present invention should have a length and flexibility such that it is capable of extending through enough of the body vessel to at least partially free the cardiac lead from the surrounding endothelial growth. For best results, the device will be structured such that torque can be transmitted by the operator from the proximal end to the "tipped" distal end of the device. In this manner, the operator need merely insert the sheath into the vessel, and thereafter direct, or torque, the sheath to the desired site to enable the tip to cut or otherwise disrupt the growth surrounding the lead.

Distal tips for lead extraction devices are known in the art, and those skilled in the art can readily select a tip for use with the extraction devices described herein. Although many such tips are effective in some instances, prior art tips often do not have the versatility to be used with a wide variety of devices, and often provide less effective cutting and/or disrupting action than desired. Accordingly, another feature of the present invention comprises novel tip structures that are intended for use in the inventive extraction devices described, as well as with other extraction and/or cutting devices that utilize cutting tips or ends.

Figure 18:
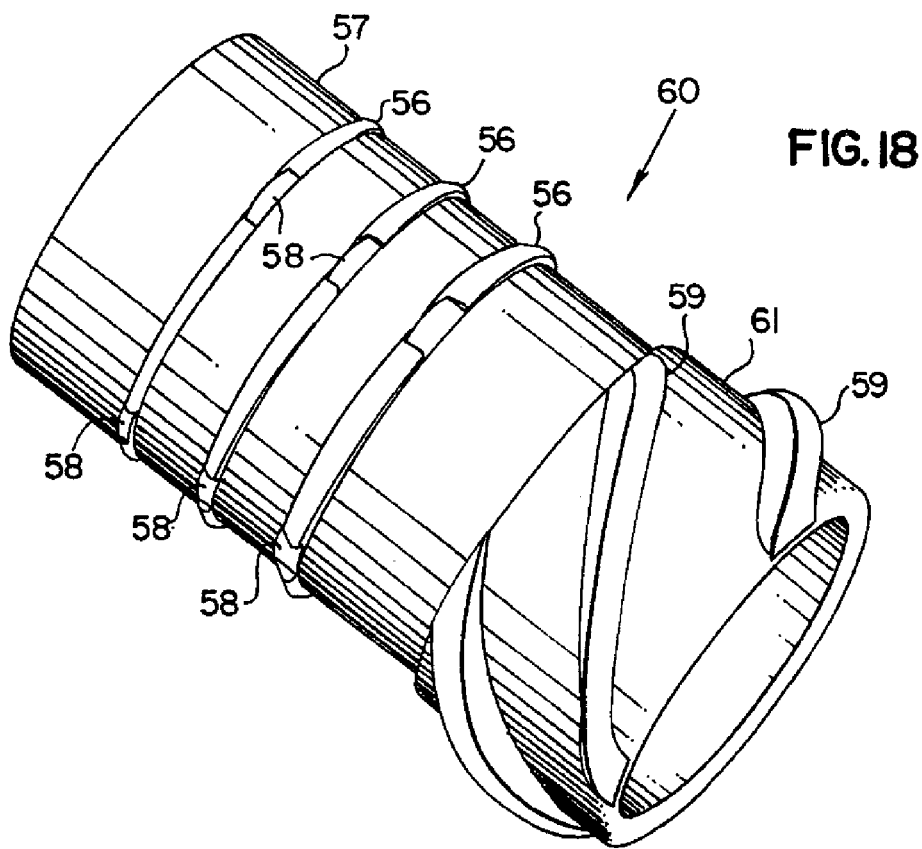
FIG. 18 is a perspective view of one embodiment of a distal tip for a lead extraction device.

FIG. 18 illustrates one embodiment of a distal tip 60 that may be joined to the distal end of a device, such as the sheath of a lead extraction device as described herein. Typically, the distal tip is bonded, adhered, or otherwise affixed to the distal end of a sheath in a secure manner, such that the tip will not disengage under normal conditions encountered during use. In one preferred embodiment, a small diameter proximal end portion 57 of tip 60 may be affixed to the inner surface at the distal end of the sheath, such as sheath 14 in the embodiment of FIGS. 1-5. Those skilled in the art will appreciate that other common means of securely affixing a distal tip to the distal end of a device, such as the sheath described herein, can be substituted.

In the embodiment of FIG. 18, small diameter proximal end portion 57 of tip 60 includes one or more optional rings 56 fitted along the outer surface of proximal end portion 57. When more than one ring is present, rings 56 are preferably aligned in order of increasing width of said ring body in the direction of the distal tip portion. Providing rings having a smaller width in the proximal direction minimizes the stresses in the sheath at the area of joinder of the sheath and the tip, where stresses resulting from tension, torsion, and bending tend to be the highest. If desired, rings 56 may be provided with one or more cut-outs 58. Cut-outs 58 serve to hinder rotation of the tip when the proximal tip portion is positioned inside the distal portion of the sheath.

Although the preferred embodiment illustrated above comprises rings 56 for engagement with the inner surface of sheath 14, those skilled in the art will appreciate that other conventional attachment mechanisms may be substituted in a particular case. For example, rather than rings, the proximal end of tip 60 can be provided with one or more barbs along the proximal length of the tip, which barbs are configured to attach to the inner surface of the sheath. As another alternative, the proximal end of tip 60 can be provided with a roughened outer surface for facilitating attachment with the inner surface of the sheath by well-known means, such as adhesion. In this case, the outer surface of the cutting tip may be roughened by any conventional process, such as bead blasting and etching. As is well known, the use of a roughened outer surface enables an improved connection to be formed between the cutting tip and the sheath.

The embodiment of FIG. 18 also illustrates a series of radially outwardly directed projections, such as helices 59, on the outer surface of tip 60. Preferably, tip 60 includes four helices 59 spaced about 90 degrees apart along the outer surface of distal end portion 61 of the tip. The radially outer projections, such as helices 59, disrupt (alter or move aside) the body tissue encountered during insertion and rotation of the lead extraction device. Preferably, the leading (distal) end of the tip is structured such that the tip primarily, if not completely, disrupts, rather than cores or cuts, enough of the obstruction in the vicinity of the lead to allow the sheath to pass through the tip. By gently disrupting the obstruction, rather than cutting or coring it, the tips have a reduced propensity to cut a lead or breach a vessel wall. Disrupting-type tips are generally preferred for use with rotary action devices. In this case, the tips disrupt the tissue in a forward direction along the path of the structure, such as a cardiac lead, targeted for removal, while at least substantially avoiding cutting in an outward or inward direction.

Although the disruptors are shown in the figure as helices, this is only one example of a type of disruptor element that may be present on the tip portion. As alternatives, the disruptor may comprise linear, or non-linear, segments of other configurations, which segments may or may not be continuous, and may have any cross-sectional dimension. Similarly, the disruptor elements may point in any direction, or in no direction, in which case the disrupter element can have a configuration such as a dot or a circle.

Figure 27:
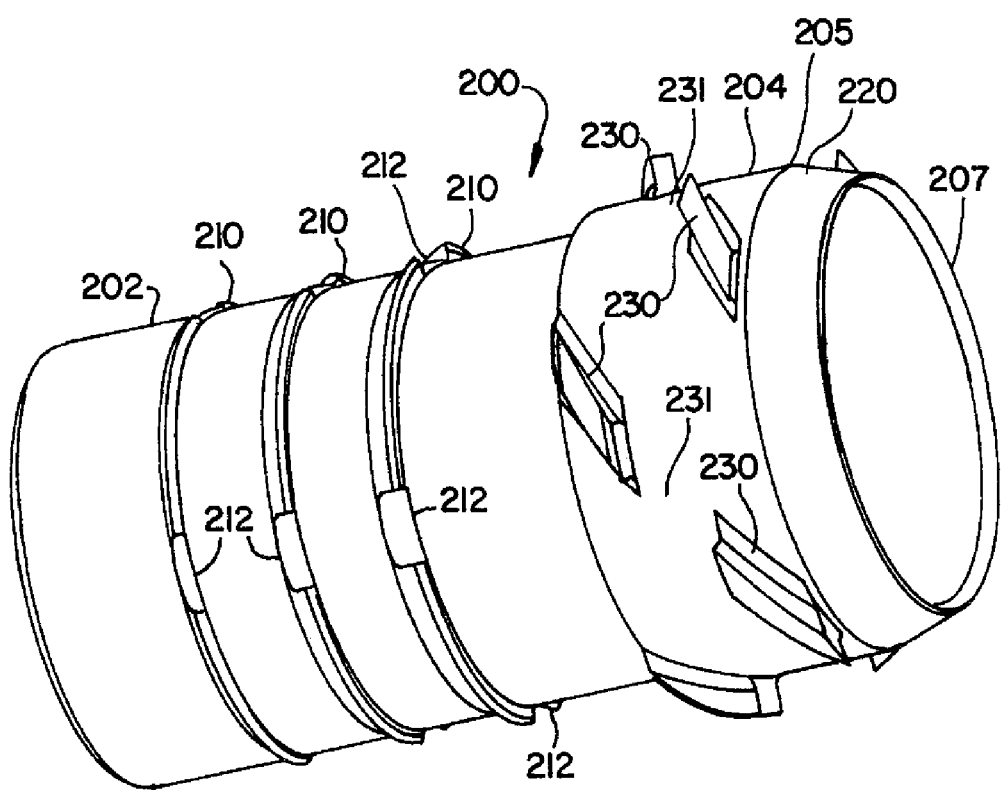
FIG. 27 is an alternative embodiment illustrating variations of the tip of FIG. 18.

FIG. 27 illustrates a variation of the tip embodiment of FIG. 18. Tip 200 is structured in a manner such that it may be bonded, adhered, or otherwise securely affixed to the distal end of a sheath, in any convenient manner. If desired, tip 200 may be structured to have a small diameter proximal end portion 202 and a larger diameter distal end portion 204. One or more optional rings 210 (with or without cut-outs 212) may be provided as before, or alternatively, other conventional attachment mechanisms, such as barbs, may be substituted in a particular case.

In the embodiment of FIG. 27, tip distal end portion 204 includes an inwardly tapered distal segment 220. Preferably, tapered segment 220 terminates in the distal direction in a rounded or otherwise generally non-traumatic distal leading edge 207. Providing a rounded or otherwise non-traumatic leading edge 207 minimizes the possibility that the leading edge may inadvertently cut through the vessel, or through the insulation of the lead as it tracks over the lead.

Helices 230 or other disrupter elements are provided at the distal end portion 204 of tip 200. Preferably, helices 230 do not extend all the way to the distal leading edge 207, but rather, begin proximal of the leading edge, and extend in the proximal direction therefrom. The leading face of helices 230 (from the distal viewpoint) may have the geometrical configuration shown in the figures, however, other configurations will also likely provide beneficial results.

In the variation shown in FIG. 27, helices 230 originate at or near the junction 205 between the non-tapered length and the tapered segment 220 of distal end portion 204, and extend proximally therefrom. Although continuous helices in the nature of helices 59 of FIG. 18 may be provided, the helices need not be continuous. The embodiment illustrated in FIG. 27 includes a variation wherein the individual helices 230 are discontinuous. By "discontinuous" is meant that an individual helix has one or more spaces, or voids, 231 along the length of the particular helix. The discontinuous helices provide the device with a heightened ability to engage surrounding scar tissue. Preferably, helices 230 extend in the proximal direction along the length of larger diameter distal end portion 204.

Figure 19:
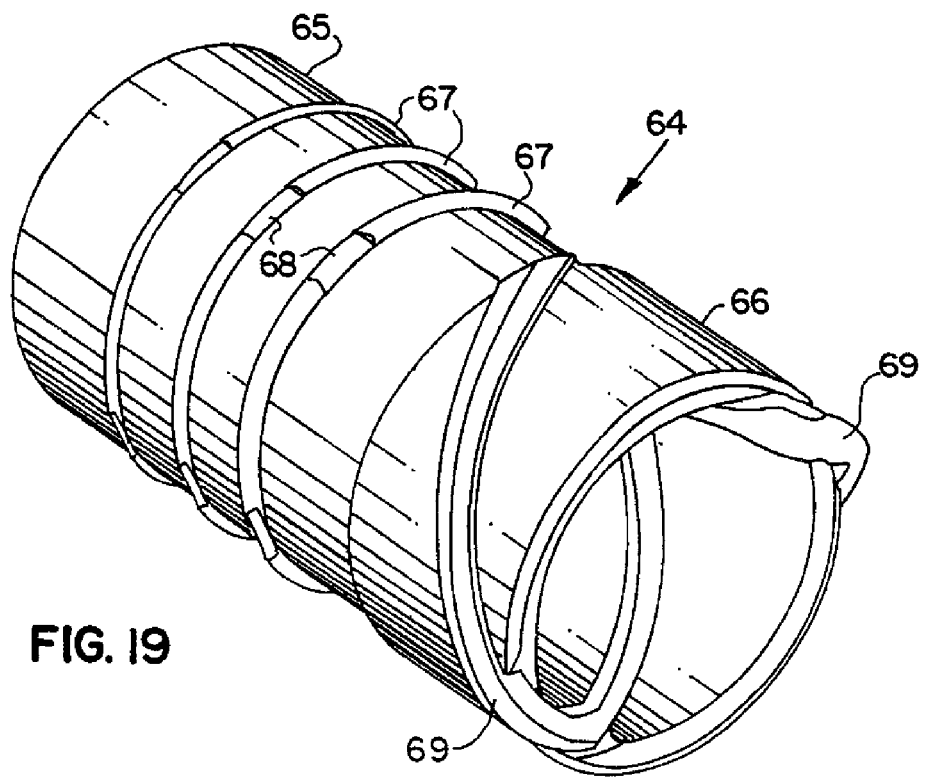
FIGS. 19-26 are perspective views of additional embodiments of a distal tip for a lead extraction device.

FIG. 19 illustrates an alternative embodiment of a tip 64 that may be affixed to the distal end of a sheath. Tip 64 may be engaged at the distal end of a sheath in the same manner as tip 60. Tip 64 includes a proximal end 65 and a distal end 66, and if desired, may include a plurality of rings 67 with or without cut-outs 68 as described. In the embodiment of FIG. 19, the disrupter elements comprise two helices 69, although more, or fewer, helices may be provided. Each helix 69 traverses at least a portion of the outer diameter of distal tip 66, across the end of the tip, and also extends along at least a portion of the inner diameter of at least the distal portion of tip 66. Similarly, if other types of disruptor elements are utilized, they may also traverse at least a portion of the inner diameter of tip 66.

Figure 20:
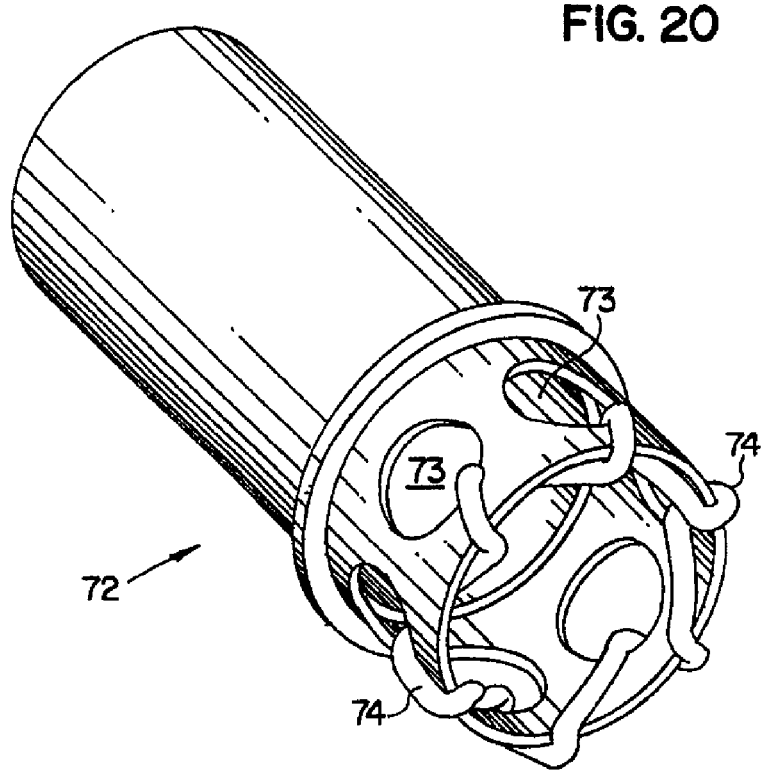

FIG. 20 illustrates another embodiment of a tip 72 that may be affixed to the distal end of a sheath. In this embodiment, a disruptor element comprises a wire formed to comprise a disrupting configuration, such as helices 74 in the embodiment shown. The wire comprising helices 74 is oriented to snake through perforations 73 in the distal portion of tip 72. Preferably, the ends of the wire are joined to each other, for example by welding, to form a continuous shape, such as a continuous toroidal helix. As shown in FIG. 20, this structure may be compressed in a manner to maximize the inner dimension available for passage of the pacing lead, and at the same time, to minimize the outer dimension which may otherwise encroach upon the body vessel. If desired, parts of the helix may also be joined (as by soldering, for example) to the body of the tip.

While disrupting the tissue, the disrupter elements urge the tissue to move in a direction which may be different from the direction of motion of the disrupter element. For example, a clockwise rotation of the tip, as viewed from the proximal end, would urge the tissue inside the tip to move in a distal direction, and the tissue at the tip to move outward (radially), for the embodiments shown in FIGS. 19 and 20. Additionally, the tissue on the outside of the tip would be urged to move in the proximal direction for the embodiments shown in FIGS. 18, 19 and 20.

Figure 21:
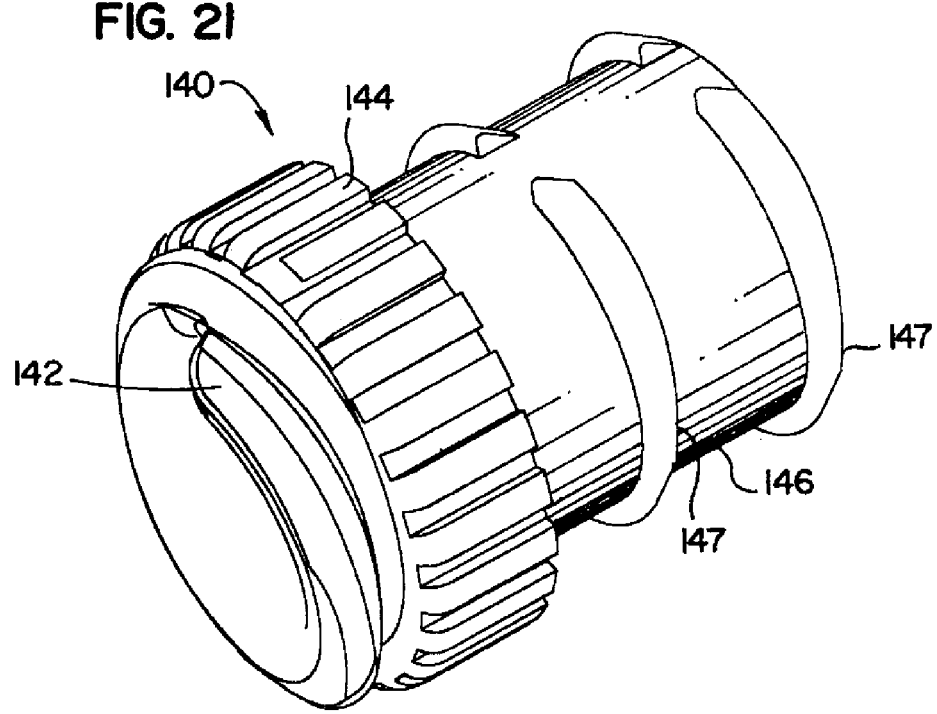

FIG. 21 illustrates another embodiment of a distal tip 140 according to the present invention. Tip 140 is capable of providing a broader, cleaner pathway through the vessel than many existing tips. Tip 140 includes a threaded distal end 142 and a larger diameter sleeve portion 144. In this embodiment, smaller diameter proximal portion 146 is sized to be affixed to the inside surface of a sheath, such as the inner sheath of a set of telescoping sheaths, in the same manner as the tips of FIGS. 18-20. If desired, small diameter portion 146 may be provided with rings 147, barbs, or other attachment structure as described previously. Preferably, threads 142 only extend incrementally a short distance, such as one or two thread turns, beyond serrated sleeve 142, and have a low profile to enable only limited threaded engagement with the obstruction. Extending the threads only a limited distance distal to sleeve 144 as shown reduces the possibility that the tip may inadvertently cut into the vessel.

Preferably sleeve 144 includes a serrated outer surface as shown in the figure. Sleeve 144 is preferably sized such that it has a slightly larger outer diameter than that of the (inner) sheath that receives proximal portion 146. This better accommodates a telescoping outer sheath, when present, and eases the advancement of the telescoping outer sheath through the area that has been opened by the tip. Advancement of the sleeve also obliterates the threaded pathway formed by the threads, thereby facilitating advancement of the device in the vessel. In addition, when the threaded pathway is obliterated in this manner, removal of the device is facilitated, since it is not necessary to reverse the threaded pathway to achieve removal.

Figure 22:
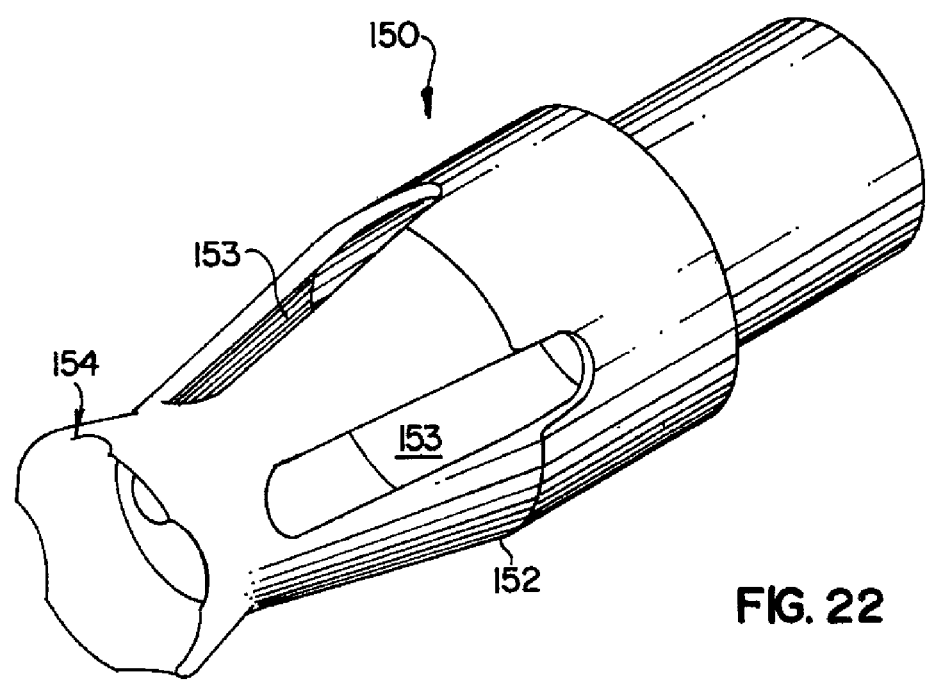
Figure 23:
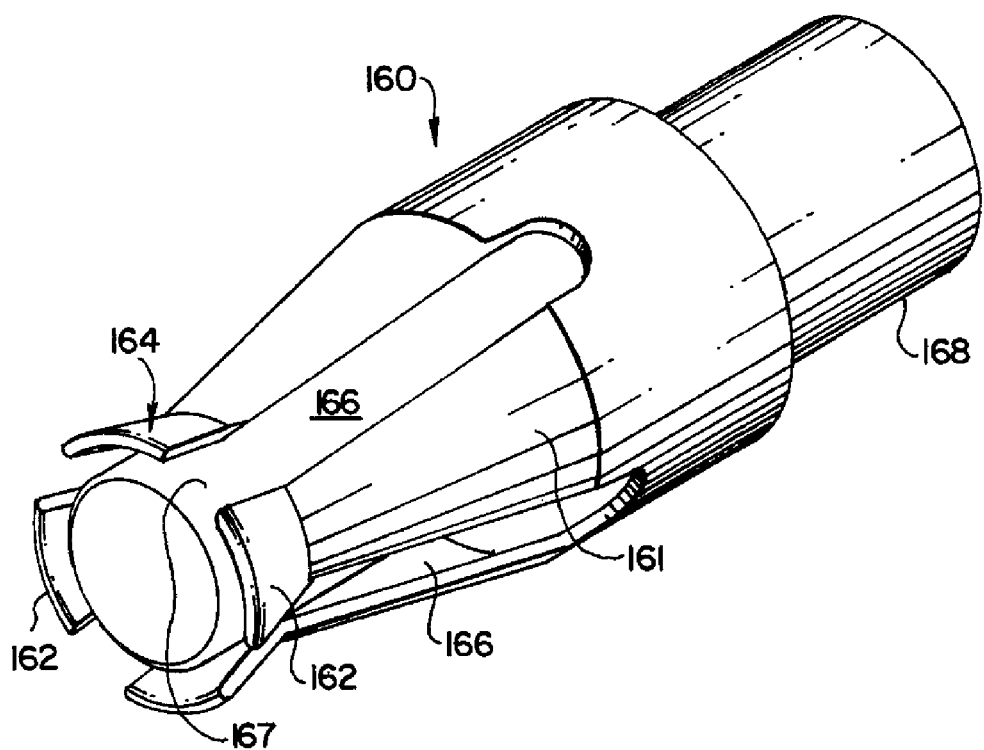

FIGS. 22 and 23 illustrate further embodiments of tips 150, 160 suitable for use with a lead extraction device. These tips are also generally referred to as disruptor tips, since the action of these tips primarily "disrupts", rather than cores of cuts, the obstruction. The tips are provided with generally non-aggressive leading ends 154, 164, respectively, which leading ends are shaped such that they disrupt (alter or move aside) enough of the obstruction in the vicinity of the lead to allow the sheath to pass through. By gently disrupting the obstruction, rather than cutting or coring it, the tips have a reduced propensity to cut a lead or breach a vessel wall. Tips 150, 160 are generally preferred for use with rotary action devices.

Tip 150 in FIG. 22 is provided with a generally horn-shaped body 152, having a plurality of longitudinal slots 153 formed therein. In the embodiment shown, horn-shaped body 152 tapers in the distal direction, wherein the terminal portion of body 152 comprises a larger-diameter fluted terminal portion 154. In a preferred embodiment, the fluted terminal portion includes gentle alternating 9 axially-extending extensions and grooves. Proximal portion 156 has a smaller diameter than that of the distal horn-shaped portion so that it may be affixed to the inside surface of a sheath in the manner discussed previously.

Tip 160 in FIG. 23 has a split tulip-shaped configuration. Petals 162 extend radially outwardly from tapered body 161. Preferably, axially-extending slots 166 are provided to assist in dilation and the movement of obstructing material. A thin-walled inner sleeve 167 is provided to ensure that the lead or lead coil cannot enter the open slot portions 166 of the tip. Similar to the fluted terminal portion of tip 150, tip 160 also includes anon-aggressive terminal portion, denoted by the petals and the sleeve, to disrupt the obstruction. Once again, proximal portion 168 is sized to be affixed to the inside surface of a sheath.

Figure 24:
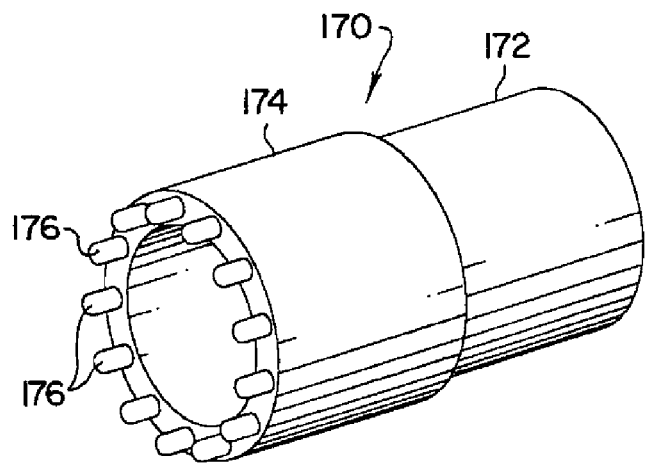
Figure 25:
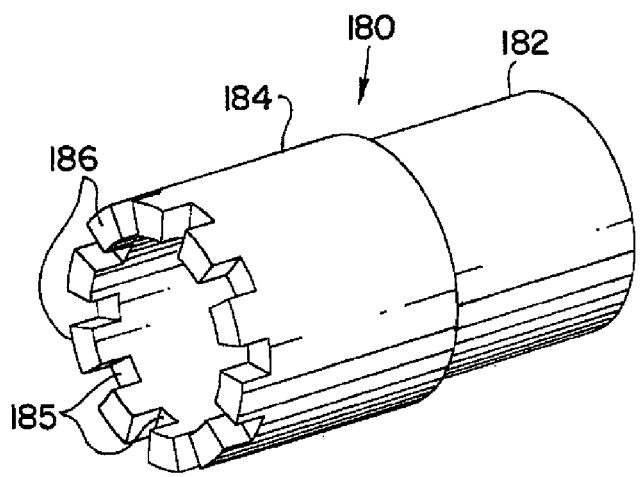
Figure 26:
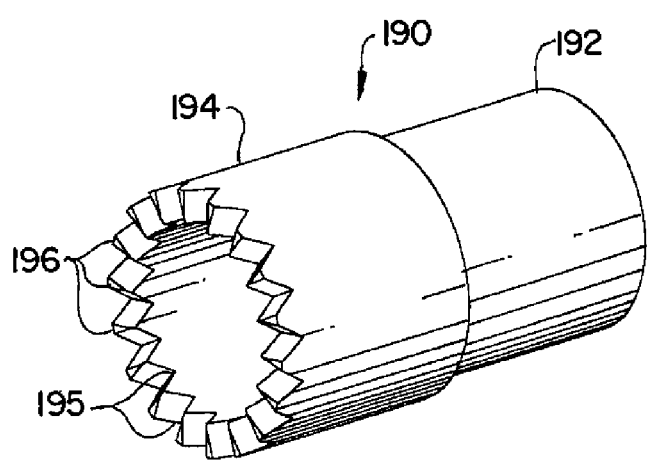

FIGS. 24-26 illustrate other alternative embodiments of tips 170, 180, 190 suitable for use with a lead extraction device. Tips 170, 180, 190 include respective smaller diameter proximal portions 172, 182, 192, and larger diameter distal portions 174, 184, 194. As described previously, the smaller diameter proximal portions are sized for affixation within the inside surface of a sheath, such as the inner sheath of a conventional set of telescoping sheaths. Tip 170 is provided with a plurality of axially extending nubs 176. The configuration of this tip lends itself well to both cutting and dilation. Tip 180 is provided with a plurality of grooves 185 disposed along a terminal portion of said distal end. In the embodiment shown, grooves 185 are disposed between alternating projections 186. Although the grooves and projections are shown as square-cornered structures, this is exemplary only, and any other configuration may be substituted. The distal end of tip 190 is shaped similar to a hole saw, with alternating tipped projections 196 and grooves 195 between adjacent projections. Tips 180, 190 are intended primarily for cutting or coring through an obstruction.

The tips illustrated in FIGS. 18-27 may be fabricated from a material having sufficient strength and rigidity to cut through or otherwise disrupt obstructions encountered during a lead removal. Metals and metal alloys, such as stainless steel, nitinol and titanium, are particularly preferred tip materials. Such tips may be formed from known techniques, such as machining and metal injection molding. In some instances it may be preferred to form the tip from two discrete sections, which sections are then combined into the finished tip. For example, in the tip of FIG. 23, it may be preferable to form the inner sleeve separately, and then combine it with the remainder of the tip by conventional means, such as soldering. Those skilled in the art can readily determine other appropriate techniques for preparing a tip within the scope of the present invention.

Those skilled in the art will appreciate that other compatible materials may be used in place of metal or metal alloys. For example, a fiber-reinforced polymer, such as fiber-reinforced polypropylene, may be used. Non-limiting examples of suitable fiber reinforcements include glass and carbon fibers. In an embodiment wherein the tip is formed as an integral portion of the sheath, the tip may conveniently be formed of a polymer, such as polypropylene, and may be molded onto the end of a sheath formed from a polymer that is compatible to the polymer of the tip material.

The inventive device may also include, or be used in combination with, other known features of medical devices. One non-limiting example is the use of the lead extraction device in combination with a tip-deflecting mechanism. As well known by those of skill in the art, a tip-deflecting mechanism is normally operated by activating a control at the proximal portion of the mechanism. Activation of the control causes the distal portion of the mechanism to deflect in a desired manner, thereby allowing the operator to preferentially curve certain areas of the device, or to change the orientation of the tip, or a portion of the tip, of the device. Thus, one possible use of the inventive device is to position the sheath and tip portion of the device inside a tip-deflecting mechanism. The sheath portion of the cutting tip rails the lead, and is deflected in accordance with the deflection of the tip-deflecting mechanism. As a variation of this embodiment, the tip-deflecting capability can simply be built into the cutting tip device, thereby eliminating the necessity to use a separate tip-deflecting mechanism.

The various sheaths described herein may be formed from conventional biocompatible materials well known for such purposes in the medical arts. Polymeric materials such polypropylene, polyurethane, polyethylene, nylon, PTFE, and the like, are believed to be particularly appropriate. Typically, such sheaths comprise an inner sheath and a telescoping outer sheath, and the inventive devices are readily adapted for use with such sheaths. If desired, a sheath can be reinforced with a coil or with a braided material. Such reinforcements are well known in the medical arts, and are typically formed from a metal or metal alloy. Preferably the striker flange and the sheath assembly flanges described hereinabove are formed from a biocompatible metal or metal alloy, such as titanium or stainless steel, or alternatively, a high impact plastic composite material. The outer housing is preferably formed from an acetal compound, or a polycarbonate material. The compositions described hereinabove are exemplary, and those skilled in the art will appreciate that other compositions may be substituted, such substitutions being within the scope of the invention.

If desired, selected portions of the lead extraction devices described herein, such as the tip portion, can be provided with means for x-ray or fluoroscopic vision. Such means are well known in the art, and may include, for example, the incorporation of a radiopaque band, or the inclusion of radiopaque particles in the selected portion. As still another alternative, the tip can be formed (in whole or in part) of a metal or metallic alloy to provide such visibility. In general, increased visibility of the tip is beneficial because it allows the operator to determine the location of the tip at a particular point in time, and also provides the operator with the ability to track the position and orientation of the tip with reference to the lead body.

Those skilled in that art will appreciate that the foregoing detailed description should be regarded as illustrative rather than limiting, and that it should be understood that it is the following claims, including all equivalents, that are intended to define the spirit and scope of this invention.

The invention claimed is:

1. A tip engaged with an elongated sheath member for extracting a pacemaker lead from an obstruction in a body vessel of a patient, said sheath member having a distal end and a passageway extending at least substantially therethrough, said tip comprising:
    a tip body having a proximal end, a distal end, and a passageway extending therethrough, said tip body proximal end engaged with said sheath member distal end such that said respective passageways are axially aligned and said pacemaker lead is extendable through said axially aligned passageways, said tip body distal end including an elongated portion having a diameter, and including a segment tapering inwardly from said elongated portion diameter toward a leading edge, said tapered segment having an outer surface decreasing linearly and terminating in said leading edge and configured to separate the pacemaker lead from the obstruction, a disruptor element disposed along an outer surface of said tip body elongated portion, the entirety of said disruptor element disposed proximal of at least said leading edge of said tapered segment along said outer surface, said disruptor element structured such that said tip disrupts said obstruction in a forward direction along a path of the tip as said tip is advanced over said pacemaker lead,
    wherein said disruptor element comprises a plurality of helices disposed along and projecting outwardly from said outer surface in a side-by-side manner, wherein said plurality of helices each comprise a pair of side faces defining a constant cross-section therebetween along the entire length thereof and a distal-most end face extending perpendicularly outwardly from the outer surface of said elongated portion, and wherein the distal-most end face of each of said helices is disposed proximal of and spaced apart from both the leading edge and a junction of a proximal terminal end of said tapered segment with said elongated portion, and
    wherein the tip body is movably disposable over a pacemaker lead disposed within the body vessel of the patient and is engagable with an obstruction within said body vessel.

2. The tip of claim 1, wherein a distal most portion of said leading edge comprises a generally rounded profile.

3. The tip of claim 1, wherein said plurality of helices extend substantially the length of said elongated portion.

4. The tip of claim 1, wherein at least one of said helices has a length and has a void along its length.

5. The tip of claim 1, wherein said tip body elongated portion comprises a larger diameter distal end, said tip body further having a smaller diameter proximal end, said smaller diameter proximal end engaged with an inner surface of said sheath member distal end.

6. The tip of claim 5, wherein said tip body smaller diameter proximal end includes an attachment member engaged with said inner surface of said sheath member distal end, said attachment member comprising a plurality of rings spaced along said tip body outer surface, said rings being aligned in order of increasing ring width in a direction of said tip distal end.

7. The tip of claim 6, wherein at least one of said rings includes a cut-out portion for inhibiting rotation of said tip relative to said sheath member.

8. The tip of claim 1, wherein the sheath member comprises an outer diameter that is equal to the diameter of the elongate portion.

9. The tip of claim 8, wherein the sheath member is movably disposable over a pacemaker lead disposed within the body vessel of the patient.

10. The tip of claim 1, wherein the distal-most end face of each of said helices is disposed within a plane that is perpendicular to a central longitudinal axis of the tip body.

11. An apparatus for extracting a pacemaker lead from an obstruction within a vessel of a patient, comprising:
    an elongate sheath member comprising a passageway sized to receive the pacemaker lead therein, the elongate sheath member being flexible to track over the pacemaker lead within the vessel, said sheath member having a distal end; and a tip disposed at the distal end of the sheath member and extending in a distal direction therefrom, said tip having a passageway extending therethrough, said tip and said elongate sheath member configured and axially aligned in said apparatus such that said pacemaker lead is extendable through said axially aligned passageways, said tip comprising an outer surface having at least one generally helical disruptor element disposed therealong and projecting outwardly therefrom, said tip having a leading edge structured and arranged for non-cutting engagement with said obstruction such that advancement of the apparatus over the pacemaker lead and into the obstruction causes the at least one disruptor element to push aside and separate the obstruction from the pacemaker lead, said tip comprising a conically shaped segment that tapers inwardly from a proximal terminal juncture and toward said leading edge, said conically shaped segment having an outer surface decreasing linearly and terminating in said leading edge, and wherein said at least one generally helical disruptor element has a constant cross-section along the entire length thereof and a distal-most end face that is spaced proximally of and apart from the proximal terminal juncture of said tapered segment, said distal-most end face projecting radially outwardly from said outer surface and being disposed radially outwardly of said conically shaped segment, wherein the elongate sheath member and the tip are each movably disposable over a pacemaker lead, and wherein the tip is engagable with an obstruction within the vessel of the patient.

12. The apparatus of claim 11, wherein said leading edge is generally rounded.

13. The apparatus of claim 11, comprising a plurality of generally helical disruptor elements, wherein at least one of said generally helical disruptor elements has a void along a length thereof and the distal-most end comprises a distal-most end face extending perpendicularly outwardly from the outer surface of said elongated portion, the distal-most end face comprising a planar surface that is entirely disposed within a plane that is perpendicular to a longitudinal axis of the tip.

14. The apparatus of claim 11, further comprising a drive member operationally engaged with said elongate sheath member for driving at least one of rotational and axial movement of said sheath member.

15. The apparatus of claim 14, wherein said leading edge is generally rounded, and each of said at least one generally helical disruptor element has a void along a length thereof.

16. The apparatus of claim 15, wherein said tip has a smaller diameter proximal end and a larger diameter distal end, said at least one generally helical disruptor element disposed along said larger diameter distal end, said smaller diameter proximal end including an attachment member engaged with an inner surface of said sheath member distal end.

17. The apparatus of claim 16, wherein said attachment member comprises a plurality of rings spaced along said tip body outer surface, said rings being aligned in order of increasing ring width in a direction of said tip distal end, and wherein at least one of said rings includes a cut-out portion structured and arranged for inhibiting rotation of said tip relative to said sheath member.

* * * * *